US006274335B1

(12) United States Patent
Goeddel et al.

(10) Patent No.: US 6,274,335 B1
(45) Date of Patent: *Aug. 14, 2001

(54) METHOD OF TREATMENT USING RECOMBINANT HUMAN TISSUE PLASMINOGEN ACTIVATOR

(75) Inventors: David V. Goeddel, Hillsborough; William J. Kohr, San Mateo; Diane Pennica, Foster City; Gordon A. Vehar, San Carlos, all of CA (US)

(73) Assignee: Genentech, Inc., South San Francisco, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/105,698

(22) Filed: Jun. 26, 1998

Related U.S. Application Data

(63) Continuation of application No. 08/487,456, filed on Jun. 6, 1995, now Pat. No. 5,869,314, which is a continuation of application No. 08/264,134, filed on Jun. 21, 1994, now Pat. No. 5,587,159, which is a continuation of application No. 08/109,698, filed on Aug. 20, 1993, now abandoned, which is a continuation of application No. 07/911,021, filed on Jul. 9, 1992, now abandoned, which is a continuation of application No. 07/489,855, filed on Mar. 2, 1990, now Pat. No. 5,185,259, which is a continuation of application No. 07/012,694, filed on Feb. 9, 1987, now abandoned, which is a division of application No. 06/483,052, filed on Apr. 7, 1983, now Pat. No. 4,766,075, which is a continuation-in-part of application No. 06/398,003, filed on Jul. 14, 1982, now abandoned, and application No. 06/374,860, filed on May 5, 1982, now abandoned.

(51) Int. Cl.$^7$ .............................. C12Q 1/56; C12N 9/48; C12N 9/64; C07H 21/02; A61K 38/48

(52) U.S. Cl. ........................ 435/13; 435/226; 435/212; 435/240.2; 435/252.3; 435/252.33; 536/23.1; 424/94.63; 424/94.64; 530/350

(58) Field of Search ................... 435/13, 226, 212, 435/240.2, 252.3, 252.33; 424/94.63, 94.64; 530/350; 536/23.1

(56) References Cited

U.S. PATENT DOCUMENTS

| | | | |
|---|---|---|---|
| 3,904,480 | 9/1975 | Hull et al. | 156/102 |
| 3,998,947 | 12/1976 | D'Hinterland et al. | 424/105 |
| 4,177,262 | * 12/1979 | Lormeau et al. | 424/105 |
| 4,245,051 | 1/1981 | Reich et al. | 435/212 |
| 4,259,447 | 3/1981 | Hafeli | 435/215 |
| 4,314,994 | 2/1982 | d'Hinterland et al. | 435/215 |
| 4,317,882 | 3/1982 | Horiguchi et al. | 435/212 |
| 4,370,417 | 1/1983 | Hung et al. | 435/212 |
| 4,505,893 | 3/1985 | Muri et al. | 424/94.64 |
| 4,766,075 | 8/1988 | Goeddel et al. | 435/240.2 |
| 4,853,330 | 8/1989 | Goeddel et al. | 435/226 |
| 5,185,259 | * 2/1993 | Goeddel et al. | 435/226 |
| 5,587,159 | * 12/1996 | Goeddel et al. | 435/94.64 |
| 5,869,314 | * 2/1999 | Goeddel et al. | 435/226 |

FOREIGN PATENT DOCUMENTS

| | | |
|---|---|---|
| 0005644 | 11/1979 | (EP) . |
| 2454809 | 4/1980 | (EP) . |
| 0023860A2 | 2/1981 | (EP) . |
| 0037687A2 | 10/1981 | (EP) . |
| 0041766 | 12/1981 | (EP) . |
| 0174835A1 | 3/1986 | (EP) . |
| 1443189 | 7/1976 | (GB) . |
| 1492959 | 11/1977 | (GB) . |
| 1551275 | 8/1979 | (GB) . |
| 2025977 | 1/1980 | (GB) . |
| 2051075A | 1/1981 | (GB) . |
| 2092154 | 8/1982 | (GB) . |
| 2176703A | 1/1987 | (GB) . |

OTHER PUBLICATIONS

Rijken et al. J. Biol. Chem. 256(13) : 7035–41, Jul. 10, 1981.*
Camiolo et al., (1971), *PSEMB*, 138:277.
Thorsen et al., (1972), *Thrombos, Diathes, haemorrh.*, 28:65.
Granelli–Piperno et al., (1978), *J. Exp. Med.*, 148:223.
Thorsen (1977), *Danish Med. Bulletin*, 24:189.
Wallen (1978), *Progress in Chem. Fibrinolysis and Thrombolysis*, 3:167.
Wilson et al., (1980), Chem. Ab., 92, No. 144679a.
Collen (1980), *Edward Kowalski Memorial Lacture Thromb. Haem.*, 43:77.
Wun et al., (1982), *Jrnl. Biol. Chem.*, 257:3276.
Kaufman et al., (1982), Gene Appliflication, pp. 245–250.
Weissmann, et al, (1982), *Phil. Trans. R. Soc. Lond.*, 299:7.
The Newswatch, (1982), *McGraw–Hill's Biotech. Newswatch*, 2:1.
Kaufman et al., (1982), *Molecule, Cell, Biol.*, 2:1304.
Rijken et al., (1980), *Thromb. Res.*, 18:815.
Wigler et al., (1980), *Proc. Natl. Acad. Sci. USA*, 77:3567.
Kaufman et al., (1982), *J. Mol. Biol.*, 159:601.
Salser et al., (1976), Prog. Nucl. Acids Res. Mol. Biol., 19:177.

(List continued on next page.)

*Primary Examiner*—Nashaat T. Nashed
*Assistant Examiner*—Tekchand Saidha
(74) *Attorney, Agent, or Firm*—Knobbe, Martens, Olson & Bear, LLP

(57) ABSTRACT

Human tissue plasminogen activator (t-PA) is produced in useful quantities using recombinant DNA techniques. The invention disclosed thus enables the production of t-PA free of contaminants with which it is ordinarily associated in its native cellular environment. Methods, expression vehicles and various host cells useful in its production are also disclosed.

14 Claims, 14 Drawing Sheets

OTHER PUBLICATIONS

Higuchi et al., (1976), *Proc. Nat. Acad. Sci. USA*, 73:3146.
McReynolds et al., (1977), J. Biol. Chem., 252:1840.
Rougeon et al., (1977), *Gene*, 1:229.
Rougeon et al., (1975), *Nucl. Acids Res.*, 2:2365.
Rabbitts (1976), *Nature*, 260:221.
Maniatis et al., (1976), *Cell*, 8:163.
O'Malley et al., (1976), *ICN–UCLA Symposium*, 5:309.
McReynolds et al., (1977), *Gene*, 2:217.
Seeburg et al., (1977), *Nature*, 270:486.
Shine et al., (1977), Nature, 270:494.
Seidman et al., (1978), Nature, 271:582.
Monahan et al., (1977), *J. Biol. Chem.*, 252:4722.
Liu et al., (1977), *Science*, 196:192.
Humphries et al., (1977), *Nucl. Acids Res.*, 4:2389.
Ullrich et al., (1977), *Science*, 196:1313.
Sim et al., (1978), *Cold Spring Harbor Symp. Quant. Biol.*, 42:933.
Villa–Komaroff, (1978), *Proc. Nat. Acad. Sci. USA*, 75:3727.
Gordon et al., (1978), *J. Biol. Chem.*, 253:8629.
Wall et al., (1978), *Nucl. Acids Res.*, 5:3113.
Wilson et al., (1978), *Nucl. Acids Res.*, 5:563.
Little et al., (1978), *Nature*, 273:640.
Cummings et al., (1978), *Nature*, 276:418.
Harpold et al., (1978), *Nucl. Acids Res.*, 5:2039.
Sobel et al., (1978), *Proc. Nat. Acad. Sci. USA*, 75:5846.
Chang et al., (1978), Nature, 275:617.
Poon et al., (1978), Nucl. Acids Res., 5:4625.
Nakanishi et al., (1978), *Proc. Nat. Acad. Sci. USA*, 75:6021.
Sippel et al., (1978), Nucl. Acids Res., 5:3275.
Wahli et al., (1978), *Dev. Biol.*, 67:371.
Lehrach et al., (1978), *Proc. Nat. Acad. Sci. USA*, 75:5417.
Schibler et al., (1978), *Cell*, 15:1495.
King et al.,(1979), *J. Biol. Chem.*, 254:6781.
Roberts et al., (1979), *Proc. Nat. Acad. Sci. USA*, 76:2153.
Lehrach et al., (1979), Biochemistry, 18:3146.
Rogers et al., (1979), Nucl. Acids Res., 6:3305.
Yamamoto et al., (1980), *J. Biol Chem.*, 255:2612.
Early et al., (1979), *Proc Nat Acad Sci USA*, 26:857.
Innis et al., (1979), *Arch. Biochem. Biophys.*, 195:128.
Gubbins et al., (1979), *Nucl. Acids Res.*, 6:915.
Sargent et al. (1979), Proc. Natl. Acad. Sci.,USA, 76:3256.
Bhat et al., (1979), *Proc. Nat. Acad. Sci. USA*, 76:3299.
Fantoni et al., (1979), *Nucl. Acids Res*, 6:3505.
Martial et al., (1979) *Science*, 205:602.
Kioussis et al., (1979), *Proc. Nat. Acad. Sci.*, 76:4370.
Ohno et al., (1980), *Biochem. Biophys. Acta.*, 606:34.
Fiddes et al., (1979), *Nature*, 281:351.
Goeddel et al., (1979), *Nature*, 281:544.
Kronenberg et al (1979), *Proc. Nat. Acad. Sci.*, 76:4981.
Roskam et al., (1979), *Nucl. Acids Res.*, 7:305.
Liebscher et al., (1980), *Gene*, 9:233.
Chan et al., (1979), *Proc. Nat. Acad. Sci.*, 76:5036.
Bell et al., (1979), *Nature*, 282:525.
Sim et al., (1979), *Cell*, 18:1303.
Tucker et al., (1979), Science, 206:1299.
Richards et al., (1979), Nucl.Acids Res , 7:1137.
Gough et al., (1980), *Proc. Nat. Acad. Sci. USA*, 77:554.
Firtel et al., (1979), *Proc. Nat. Acad. Sci. USA*, 76:6206.
Adams et al., (1980), *Biochemistry*, 19:2711.
Gough et al., (1980), Biochemistry, 19:2702.
Obata et al., (1980), *Gene*, 9:87.
Katcoff et al., (1980), *Proc. Nat. Acad. Sci. USA*, 77:960.
Joho et al., (1980), *Proc. Nat. Acad. Sci. USA*, 77:1106.
Wieringa et al., (1979), *Nucl. Acids Res.*, 7:2147.
Merlino et al., (1980), *Proc. Nat. Acad. Sci. USA*, 77:765.
Calame et al., (1980), *Nature*, 284:452.
Taniguchi et al., (1979), *Proc. Japan Acad* , 55:464.
Hoeijmakers et al., (1980), *Gene*, 8:391.
Law et al., (1980), *Gene*, 10:53.
Meyuhas et al., (1980), *Gene*, 10:113.
Griffin–Shea et al., (1980), *Cell*, 19:915.
Cleveland et al., (1980), *Cell*, 20:95.
Matthyssens et al., (1980), *Nucl. Acids Res.*, 8:702.
Nagata et al., (1980), *Nature*, 284:316.
Cooke et al., (1981), *J. Biol. Chem.*, 256:4007.
Cooke et al., (1980), *J. Biol. Chem.*, 255:6502.
Dunnick et al., (1980), *Nucl. Acids Res.*, 8:1475.
Vamvakopoulos et al., (1980), *Proc. Nat. Acad. Sci. USA*, 77:3149.
Auffray et al., (1980), *Nucl.Acids Res.*, 8:1231.
Deacon et al., (1980), *Nucl Acids Res.*, 8:1187.
Norgard et al., (1980), *J. Biol. Chem.*, 255:7665.
Nilson et al., (1980), *Nucl. Acids Res.*, 8:1561.
Tsitilou et al., (1980), *Nucl. Acids Res.* 8:1987.
Gorecki et al., (1980), *Proc. Nat. Acad. Sci. USA*, 77:3686.
Hobart et al., (1980), *Nature*, 288:137.
Sures et al., (1980), *Science*, 208:57.
Derynck et al., (1980), *Nature*, 285:542.
Fiddes et al., (1980), *Nature*, 286:684.
Richards et al., (1980), *J. Biol. Chem.*, 255:9306.
Schwartz et al., (1980), *Biochem.*, 19:5883.
Schibler et al., (1980), *J. Mol. Biol.*, 142:93.
Liao et al., (1980), *J. Biol. Chem.*, 255:8046.
Taniguchi et al., (1980), *Proc. Nat. Acad. Sci. USA*, 77:4002.
Ordahl et al., (1980), *Proc. Nat. Acad. Sci. USA*, 77:4519.
Amara et al., (1980), *Proc. Nat. Acad. Sci. USA*, 77:4444.
Miller et al., (1980), *J. Biol. Chem.*, 255:7521.
Chandra et al., (1980), *Biochem. Biophys. Res. Commun.*, 95:197.
Christophe et al., (1980), *Eur. J. Biochem.*, 111:419.
Zakut et al., (1980), *Nucl. Acids Res.*, 8:3591.
Hobart et al., (1980), *Science*, 210:1360.
MacGillivray, (1980), *Proc. Nat. Acad. Sci. USA*, 77:5153.
Dolby et al., (1980), *Proc. Nat. Acad. Sci. USA*, 77:6027.
MacDonald et al., (1980), Nature, 287:117.
Fagan et al., (1981), J. Biol. Chem., 256:520.
Streuli et al., (1980), Science, 209:1343.
Ginzburg et al., (1980), *Nucl. Acids Res.*,8:3553.
Cozens et al., (1980), *Eur. J. Biochem.*, 112:443.
Goeddel et al., (1980), *Nature*, 287:411.
Medford et al., (1980), *Proc. Nat. Acad. Sci. USA*, 77:5749.
Richards et al., (1981), *J. Biol. Chem.*, 256:526.
Odink et al., (1981), *J. Biol. Chem.*, 256:1453.
Bedbrook et al., (1980), *Nature*, 287:692.
Miller et al., (1980), *Endocrinology*, 107:851.
Goodman et al., (1980), *Proc. Nat. Acad. Sci. USA*, 77:5869.
Sun et al., (1981), *Nature*, 289:37.
Auffray et al., (1980), *Gene*, 12:77.
Minty et al., (1981), *J. Biol. Chem.*, 256:1008.
Ploegh et al., (1980), *Proc. Nat. Acad. Sci. USA*, 77:6081.
Maeda et al., (1980), *Proc. Nat. Acad. Sci. USA*, 77:7010.
Durnam et al., (1980), *Proc. Nat. Acad. Sci. USA*, 77:65ll.
Sullivan et al., (1981), *Nature*, 289:516.
Goeddel et al., (1980), *Nucl. Acids Res.* 8:4057.
Zernik et al., (1980), *Cell*, 22:807.
Agarwal et al., (1981), *Jrnl. Biol. Chem.*, 256:1023.

Weissenbach et al., (1980), *Proc. Nat. Acad. Sci. USA*, 77:7152.
Mather et al., (1981), *Cell*, 22:269.
Sood et al., (1981), *Proc. Nat. Acad. Sci. USA*, 78:616.
Ratzkin et al., (1981), *Proc. Nat. Acad. Sci. USA*, 78:3313.
Kurtz et al., (1981), *Gene*, 13:145.
Sargent et al., (1981), *Proc. Nat. Acad. Sci. USA*, 78:243.
Mansson et al., (1981), *Nucl. Acids Res.* 9:935.
Negishi et al., 1981), *Proc. Nat. Acad. Sci. USA*, 78:800.
Valenzuela et al., (1981), *Nature*, 289:650.
Hall et al., (1981), *Nucl. Acids Res.*, 9:65.
Craig et al, (1981), *Biochem. J.*, 194:989.
Derman et al., (1981), *Cell*, 23:731.
Goeddel et al., (1981), *Nature*, 290:20.
Nakhasi et al., (1981), *Proc. Nat. Acad. Sci. USA*, 78:834.
Demyanov et al., (1981), *Dokl–Biochem. Sect.* (*English Transl* ), 256:35.
Keshet et al., (1981), *Nucl. Acids. Res.*, 9:19.
Hagenbuechle et al., (1981), Nature, 289:643.
Pays et al., (1980), *Nucl. Acids Res.*, 8:5965.
Bothwell et al., (1981), *Nature*, 290:65.
Chung et al., (1981), *Proc. Nat. Acad. Sci. USA*, 78:1466.
Law et al., (1981), *Nature*, 291:201.
Dugaiczyk et al.,(1982), *Proc. Natl. Acad. Sci. USA*, 79:71.
Wallace, et al., (1981), *Nucl. Acids Res.*, 9:879.
Brown et al., (1981), *Proc. Nat. Acad. Sci. USA*, 78:1755.
Jacobs et al., (1981), *Science*, 213:457.
Mushinski et al, (1980), *Proc. Nat. Acad. Sci.*, USA, 77:7405.
Munjaal et al., (1981), *Proc. Nat. Acad. Sci. USA*, 78:2330.
Wieringa et al., (1981), *Nucl. Acids Res.* 9:489.
Steinmetz et al., (1981), *Cell*, 24:125.
Bothwell et al., (1981), *Cell*, 24:625.
Bozzoni et al., (1981), *Nucl. Acids Res.* 9:1069.
Hudson et al., (1981), *Nature*, 291:127.
Lewis et al., (1981), *Nucl. Acids Res.* 9:1311.
Fujii–Kuriyama et al. (1981), *J. Biochem.* , 89:1869.
Gedamu et al., (1981), *Nucl. Acids Res.* 9:1463.
Parnes et al., (1981), *Proc. Nat. Acad. Sci. USA*, 78:2253.
Auffray et al., (1981), *Gene*, 13:365.
Tosi et al., (1981), *Nucl. Acids Res* 9:2313.
Kuist et al., (1981), *Proc. Nat. Acad. Sci. USA*, 78:2772.
Lin et al., (1981), *Proc. Nat. Acad. Sci. USA*, 78:2825.
Bruskin et al., (1981), *Dev. Biol.*, 87:308.
Umeda et al., (1981), *Proc. Nat. Acad. Sci. USA*, 78:2843.
Unterman et al., (1981), *Proc. Nat. Acad. Sci. USA*, 78:3478.
Tomarev et al., (1982), *Dokl–Biochem. Sect.* (*English Transl.*) 263:117.
Gonzalez et al., (1981),*J. Biol. Chem.*, 256:4697.
Chan et al., (1981), *J. Biol. Chem.*, 256:7595.
Myers et al., (1981), *Proc. Nat. Acad. Sci. USA*, 78:3516.
Weaver et al., (1981), *Proc. Nat. Acad. Sci. USA*, 78:4073.
Stolarsky, et al., (1978), *Jrnl. Biol. Chem.*, 253:7194.
Berger et al., (1981), *J. Biol. Chem.*, 256:7006.
Jagodzinski et al., (1981), *Proc. Nat. Acad. Sci. USA*, 78:3521.
Lis et al., (1981), *Gene*, 15:67.
Land et al., (1981), *Nucl. Acids Res.*, 9:2251.
Crabtree et al., (1981), *J. Biol. Chem.*, 256:9718.
Affara et al., (1981), *Nucl. Acids Res.* 9:3061.
Sogawa et al., (1981), *J. Biol. Chem.*, 256:12561.
Lemischka et al., (1981), *J. Mol. Biol.*, 151:101.
Roninson et al., (1982), *Cell*, 28:515.
Roninson et al., (1981), Proc. Nat. Acad. Sci. USA, 78:4782.
Miller et al., (1981), DNA, 1:37.
Dodemont et al., (1981), Proc. Nat. Acad. Sci. USA, 78:5320.
Chin et al., (1981), Proc. Nat. Acad. Sci. USA, 78:5329.
Dandekar et al.,(1981), Proc. Nat. Acad. Sci. USA, 78:4853.
Crampton et al., (1981), *Nucl. Acids Res.*, 9:3821.
MacLeod (1981), *Nucl. Acids Res.*, 9:2675.
Lee et al., (1981), *Proc. Nat. Acad. Sci. USA*, 78:4922.
Ricca et al., (1981), *J. Biol. Chem.*, 256:10362.
Sasavage et al., (1982), *J. Biol. Chem.*, 257:678.
Su et al., (1981), *J. Biol. Chem.*, 256:11826.
Heidmann et al., (1981), *Proc. Nat. Acad. Sci. USA*, 78:5802.
Clissold et al., (1981), *Gene*, 15:225.
Nickerson et al., (1982), *FEBS Lett.*, 144:289.
Suggs et al, (1981), Proc. Nat. Acad. Sci. USA, 78:6613.
Suggs et al., (1981), *JCN–UCLA Symposium*, 23:683.
Westley et al., (1981), *Nucl.Acids Res.* 9:3557.
Allison et al., (1981), *Biochem. J.*, 199:725.
Nishimori et al., (1981), J. Biochem. 90:901.
Rougeon et al., (1981), *Proc. Nat. Acad. Sci. USA*, 78:6367.
Panthier et al., (1982), *Nature*, 298:90.
Fuchs et al., (1981), *Cell*, 27:75.
Cato et al., (1981), *Gene*, 16:27.
Reyes et al., (1981), *Immunogenetics*, 14:383.
Vanin et al., (1981), *Gene*, 16:141.
Kalinyak et al., (1982), *J. Biol. Chem.*, 257:523.
Broglie et al., (1981), Proc. Nat. Acad. Sci. USA, 78:7304. pg,60
Persico et al., (1981), *Nature*, 294:778.
Tucker et al., (1981), *Proc. Nat. Acad. Sci. USA*, 78:7684.
Richards et al., (1982), *J. Biol. Chem.*, 257:2758.
Kurachi et al., (1981), *Proc. Nat. Acad. Sci. USA*, 78:6826.
Hendy et al., (1981), *Proc. Nat. Acad. Sci. USA*, 78:7365.
Quinto et al., (1982), *Proc. Nat. Acad. Sci. USA*, 79:31.
Cosman et al., (1982), *Nature*, 295:73.
Lawn et al., (1981), *Nucl. Acids Res.* 9:6103.
McDonald et al., (1982), *Biochemistry*, 21:1453.
Christophe et al., (1982), *Eur. J. Biochem.*, 122:461.
King et al., (1982), *Science*, 215:985.
Lee et al., (1982), *Proc. Nat. Acad. Sci. USA*, 79:545.
Mbikay et al., (1981), Biochem. Biophys. Res. Commun., 103:825.
Davies et al., (1982), *Proc. Nat. Acad. Sci. USA*, 79:335.
Lund et al., (1981), *J. Biol. Chem.*, 256:6515.
Edens et al., (1982), *Gene*, 18:1.
Himeno et al., (1982), *J. Biol. Chem.*, 257:4669.
Chandra et al., (1981), *Biochem. Biophys. Res. Commun.*, 103:751.
Morandf et al., (1982), *J. Mol. Biol.* 156:583.
Ruiz–Varquez et al., (1982), *Nucl Acids Res.*, 10:2093.
Yoo et al., (1982), *Proc. Nat. Acad. Sci. USA*, 79:1049.
Noyes et al., (1979), Proc. Natl. Acad. Sci. USA, 76:1770.
Noda et al., (1982), *Nature*, 295:202.
Mahdavi et al., (1982), *Nature*, 297:659.
Tomarev et al., (1982), *Gene*, 17:131.
Gonzalez et al., (1982), *J. Biol. Chem.*, 257:5962.
Hellman et al., (1982), *Proc. Nat. Acad. Sci. USA*, 79:1264.
Berge–Lefranc (1981), *Eur. J. Biochem.*, 120:1.
Wiman et al., (1982), *Proc. Nat. Acad. Sci. USA*, 79:1703.
Forde et al., (1981), Nucl. Acids Res. 9:6689.
Schoenberg et al., (1981), *Nucl. Acids Res.* 9:6669.

Hastings et al., (1982), Proc. Nat. Acad. Sci. USA, 79:1553.
Gray et al., (1982), Nature, 295:503.
Land et al., (1982), Nature, 295:299.
Inana et al., (1982), J. Biol. Chem., 257:9064.
Lalanne et al., (1982), Nucl. Acids Res 10:1039.
Robert et al., (1982), Proc. Nat. Acad. Sci. USA, 79:2437.
Oychinnikoy et al., (1982), Dokl–Biochem. Sect. (English Transl.).
Morris et al., (1982), J. Biol. Chem., 257:3225.
Tyler et al., (1982), Proc. Nat. Acad. Sci. USA, 79:2008.
Brennand et al., (1982), Proc. Nat. Acad. Sci. USA, 79:1950.
Di Lauro et al (1982), Gene, 19:117.
Heidmann et al., (1982), Nucl. Acids. Res. 10:1535.
Haley et al., (1982), DNA, 1:155.
Hennighausen et al., (1982), Eur. J. Biochem., 125:131.
Cubler et al., (1982), Nature, 295:206.
Comb et al., (1982), Nature, 295:663.
Hieber (1982), Biochem. Biophys. Res. Commun., 104:1271.
Korman et al., (1982), Proc. Nat. Acad. Sci. USA, 79:1844.
Fujii–Kuriyama et al (1982), Prim. Tertiary Struct. Nucl. Acids Cancer Res., pp. 31–40.
Krieg et al., (1982), Nucl. Acids Res., 10:1495.
Godine et al., (1982), Jrnl. Biol. Chem., 257:8368.
Chebath et al., (1982), Molec. Biol Rep. 8:149.
Shinohara et al., (1982), Proc. Natl. Acad. Sci. USA, 79:2783.
Fujii–Kuriyama et al., (1982), Proc. Natl. Acad. Sci. USA, 79:2793.
Sims et al., (1982), Science, 216:309.
Lieman–Hurwitz et al., (1982), Proc. Natl. Acad. USA, 79:2808.
Gerlach et al., (1982), Proc. Natl. Acad. Sci. USA, 79:2981.
Glover et al., (1982), Proc. Natl. Acad. Sci. USA, 79:2947.
Reyes et al., (1982), Proc. Natl. Acad. Sci. USA, 79:3270.
Amara et al., (1982), Nature, 298:240.
Gustafsson et al., (1982), Scand. J. Immunol., 16:303.
Pedersen et al., (1982), Cell, 29:1015.
Garfinkel et al., (1982), Jrnl. Biol. Chem., 257:11078.
Karin et al., (1982), Nucl. Acids Res., 10:3165.
Hennighausen et al., (1982), Nucl. Acids Res., 10:2677.
Alexander et al., (1982), Proc. Natl. Acad. Sci. USA, 79:3260.
Bothwell et al., (1982), Nature, 298:380.
MacDonald et al., (1982), Jrnl. Biol. Chem., 257:9724.
Skup et al., (1982), Nucl. Acids Res., 10:3069.
Lamouroux et al., (1982), Proc. Natl. Acad. Sci. USA, 79:3881.
Minth et al., (1982), Jrnl. Biol. Chem., 257:10372.
Devos et al., (1982), Nucl. Acids Res., 10:2487
Harris et al., (1982), Nucl. Acids Res., 10:2177.
Kakidani et al., (1982), Nature, 298: 245.
Dandekar et al., (1982), Proc. Natl. Acad. Sci. USA, 79:3987.
Turner et al., (1982), Nucl. Acids Res., 10:3769.
Kraus et al., (1982), Proc. Natl. Acad. Sci. USA, 79:4015.
Balliyet et al., (1982), Proc. Natl. Acad. Sci. USA, 79:4466.
Wetekam et al., (1982), Gene, 19:179.
Shen et al., (1982), Proc. Natl. Acad. Sci. USA, 79:4575.
Menne et al., (1982), Proc. Natl. Acad. Sci. USA, 79:4853.
Derynck et al., (1982), Nucl. Acids Res., 10:3605.
Shiosaka et al., (1982), Proc. Natl. Acad. Sci. USA, 79:4668.
Robson et al., (1982), Proc. Natl. Acad. Sci. USA, 79:4701.
Moir et al., (1982), Gene, 19:127.
Giraudat et al., (1982), EMBO Jrnl., 1:713.

Heyneker et al., (1982), Genetics of Industrial Microorganisms pp. 214–221.
Woods et al., (1982), Proc. Natl. Acad. Sci. USA, 79:5661.
Stetler et al., (1982), Proc. Natl. Acad. Sci. USA, 79:5966.
Sinha et al., (1982), Proc. Natl. Acad. Sci. USA, 79:5847.
Kenten et al., (1982), Proc. Natl. Acad. Sci. USA, 79:6661.
Hoffman et al., (1982), Nucl. Acids Res., 10:7819.
Luskey et al., (1982), Proc. Natl. Acad. Sci. USA, 79:6210.
Noda et al., (1982), Nature, 299:793.
Schuler et al., (1982), Nucl. Acids Res., 10:8245.
Brooker et al., (1982), Eur. J. Biochem., 129:325.
Krieg et al., (1982), Nucl. Acids Res., 10:6777.
Konecki et al., (1982), Nucl. Acids Res., 10:6763.
Wake et al., (1982), Proc. Natl. Acad. Sci. USA, 79:6979.
Breslow et al., (1982), Proc. Natl. Acad. Sci. USA, 79:6861.
Liu et al., (1982), Proc. Natl. Acad. Sci. USA, 79:7852.
B ock et al., (1982), Nucl. Acids Res., 10:8113.
Chin et al., (1982), Proc. Natl. Acad. Sci. USA, 79:7704.
Breslow et al., (1982), Jrnl. Biol. Chem., 257:14639.
Degen et al., (1986), Jrnl. Biol. Chem., 261:6972.
Harris et al., (1986), Mol. Biol. Med., 3:279.
Lemontt et al., (1985), DNA, 4:419.
Browne et al., (1985), Gene, 33:279.
Zonneveld et al., (1985), Biochem. J., 235:385.
Bilofsky et al., (1986), Nucl. Acids Res., 14:1.
Higashi et al., (1983), J. Biol. Chem., 258:9522.
Persico et al., (1986), Nucl. Acids Res., 14:2511.
Martini et al., (1986), EMBO J., 5:1849.
Opdenakker et al., (1983), Eur. J. Biochem., 131:481.
Okayama and Berg, (1982), Mol. Cell. Biol., 2:161.
Wallace et al., (1979), Nucl. Acids Res., 6:3543.
Wallace et al., (1981), Nucl. Acids Res., 9:879.
Wood et al., (1985), Proc. Natl. Acad. Sci. USA, 82:1585.
Davis et al., (1980), Adv. Bact. Genetics, pp. 220–221.
Szostak et al., (1979), Methods Enzymol., 68:419.
Wahl et al., (1987), Methods Enzymol., 152:399.
Riggs et al., (1980), Recent Progress in Hormone Res., 36:261.
Montgomery et al., (1978), Cell, 14:673.
U.S. Patent application Ser. No. 368,773, Filed Apr. 15, 1982.
Diamond et al., (1980), Adv. Cancer Res., 32:41.
Goldfarb et al., (1980), Biochemistry, 19:5463, No. 24.
Wilson et al., (1979), Cancer Research, 39:1579.
Goldfarb et al., (1978), Cancer Research, 38:4601.
Christman et al., (1978), Cancer Research, 38:3854.
Vassalli et al., (1977), Cell, 11:695.
Wigler et al., (1976), Nature, 259:232.
Jaken et al., (1981), J. of Cell Biol., 90:727.
Jaken et al., (1981), Biochemical and Biophysical Research Communications, 99:379, No. 2.
Ny et al. (1984), Proc.Natl.Acad.Sci.,USA, 81:5355.
Tilghman et al., (1979), J. Biol. Chem., 254:7393.
Cochet et al., (1979), Nucl. Acids Res., 6:2435.
Buell et al., (1979), J. Biol. Chem., 254:9277.
Wahl et al., (1979), J. Biol. Chem., 254:8679.
Hoylaerts et al., J.B.C. 257, No. 6, 2912–2919 (1982).
Weimar et al., The Lancet 2, 1018–1020 (Nov. 7, 1981).
Wiman et al., Nature 272, No. 5648, 549–550 (Mar. 2, 1978).
Allen, Cell Biol. Int. Rep., 4(9), 803 (1980) Chemical Abstracts, vol. 93, 183281e, p. 396 (1980).
Angles–Cano et al., C.R. Acad. Sc. Paris, 289, p. 485 (1979) Chemical Abstracts, vol. 92, 36746m (1980).

Aoki, J. Biochem. 75, p. 731 (1974).
Astrup et al., Arch. Biochem. Biophys. 40, 346–351 (1952).
Barlow et al., Proc. Serono Symp. 9 (1977) Chem. Abstracts 89, No. 7, 57188j. p. 360 (1978).
Binder et al., J. of Biol. Chem. 254, p. 1998 (1979).
Christman et al., Proteinases in Mammalian Cells & Tissues (A.J. Barrett, ed.) pp. 91–149 (Elsevier, Amsterdam).
Danø et al., J. Exp. Med. 147(3) pp. 745–757 (1978) Chem. Abstracts 88, No. 21 (1978) 150159q.
Danø et al., Biochim. et Biophys. Acta, 613, p. 542 (1980) Chem. Abstracts 93, p. 260 (1980) 90924b.
Fraki et al., J. Cutaneous Pathol. 6(3) pp. 195–200 (1979) Chem. Abstracts 92, No. 1, 4445w (1980).
Heussen et al., Analytical Biochem. 102, p. 196–202 (1980) Chem. Abstracts 92, 89750q (1980).
Ouchterlony, Progress in Allergy, vol. V (P. Kallos, ed.) p. 1–78.
Petrenko, Purification & Properties of Plasminogen Activator from Human Blood Plasma after Sudden Death (Trans. from Biokhimiya—Moscow) 43(8) 1978.
Petrenko, Chem. Abstracts, vol. 89, 192926p (1978).
Porath et al., Nature 258, p. 598–599 (1975).
Pye et al., Proc. Serono Symp. 9 (Throm. Urokinase) p. 43–58 (1977)—Chem. Abstracts 89, 159241p. p. 217 (1978).
Radcliffe et al., Archives of Biochem. & Biophys. 189, 185 (1978).
Rijken et al., Plasminogen Activator from Human Tissue (Gaiboia Omstotite. HRO TMO p. 1–125).
Roblin et al., Can. Research, 40, p. 2706–2713 (1980) Chem. Abstracts 93(13), 126098b (1980).
Shiba et al., Chem. Abstracts, vol. 89, 103261c (1978(.
Sumitomo Chemical Co., Jap. Kokai 79/147993: Chem. Abstracts 92 (13), 106531p (1980).
Vermylen et al., Clin. Chim Acta, 8, 418–424 (1963).
Vetterlein et al., J. Biol. Chem., 254, p. 575–578 (1979) Chem. Abstracts 90, (17) 135631k (1979).
Wang et al., Cancer Research, 40(2), p. 288–92 (1980) Chem. Abstracts 92(11) 92449d.

Weber & Osborn, J. Biol. Chem., 244, p. 4406–4412 (1969).
Wilson et al., Cancer Research, 40, p. 933–938 (1980).
Wu et al., Int. J. Biochem., vol. 10, p. 1001–1006 (1979) Chem. Abstracts 92, 54020z (1980).
Rijken, D.C. et. al. *J. of Biol. Chem.*, vol. 256(13), pp. 7035–7041 (1981).
Rijken, D.C. et. al. *Biochem. Bioph s. Acta*, vol. 580, pp. 140–153 (1979).
Bollen, A. *Biochem. Bioph s. Res. Comm.*, vol. 97(1), pp. 207–215 (1980).
Edlund, T. et. al. *Proc. Natl. Acad. Sci.*, vol. 80, pp. 349–352 (1983).
Pennica, D. et. al. *Nature*, vol. 301, pp. 214–221 (1983).
Opdenakker, H. et. al., *Eur. J. Biochem.*, vol. 121, 269–274, 1982.
Ringold, G. et. al., *J. Mol. Appl. Genet.* 1(3), 165–75, 1982; *Chem. Abst.* 96:17531p. 1982.
O'Hare, et. al., *Proc. Natl. Acad. Sci.*, vol. 78(3) 1527–31, 1981.
Martial, J. et. al., *Science*, vol. 205, 602–607, 1979.
*Gene Expression*, vol. 2, Lewin, B(Ed.) p. 148–153, 1974.
Ordahl, C. et. al., *Proc. Natl. Acad. Sci.*, vol. 77, No. 8, p. 4519–4523, 1980.
*Molecular Cloning* (Maniatis, Fritsch & Sambrook, Eds.), Cold Spring Harbor Laboratory, pp. 224–228, 1982.
Heyneker, H. et. al., *Proc. of IVth Internat'l Symposium on Genetics of Industrial Microorganisms* (Eds. Ikeda & Beppu), p. 214–221, 1982.
Ratzkin, B. et al., *Proc. Natl. Acad. Sci.*, vol. 78, No. 6, p. 3313–3317, 1981.
*Genetic Engineering Ltr.*, vol. 2 No. 7 (Fishbein, G. Publisher) Sep. 10, 1982.
*Biotechnology News*, vol. 3 No. 5, Mar. 1, 1983.
*Genetic Engineering News*, p. 24, Mar. 1985.
Sargent, T. et. al., *Proc. Natl. Acad. Sci.*, vol. 78, No. 1, p. 243–246, Jan. 1981.

* cited by examiner

```
GTTCTGAGCACAGGGCTGGAGAGAAAACCTCTGCGAGGAAAGGGAAGGAGCAAGCCGTGA
```

```
                                      -35                    -30
                                      met asp ala met lys arg gly leu
ATTTAAGGGACGCTGTGAAGCAATC             ATG GAT GCA ATG AAG AGA GGG CTC
```

```
                              -20
cys cys val leu leu leu cys   gly ala val phe val ser pro ser
TGC TGT GTG CTG CTG CTG TGT   GGA GCA GTC TTC GTT TCG CCC AGC
```

```
        -10                                                   1
gln glu ile his ala arg phe arg arg gly ala arg   SER TYR GLN
CAG GAA ATC CAT GCC CGA TTC AGA AGA GGA GCC AGA   TCT TAC CAA
```

```
                              10
VAL ILE CYS ARG ASP GLU LYS  THR GLN MET ILE TYR GLN GLN HIS
GTG ATC TGC AGA GAT GAA AAA  ACG CAG ATG ATA TAC CAG CAA CAT
```

```
       20                                             30
GLN SER TRP LEU ARG PRO VAL LEU ARG SER ASN ARG VAL GLU TYR
CAG TCA TGG CTG CGC CCT GTG CTC AGA AGC AAC CGG GTG GAA TAT
```

```
                              40
CYS TRP CYS ASN SER GLY ARG ALA GLN CYS HIS SER VAL PRO VAL
TGC TGG TGC AAC AGT GGC AGG GCA CAG TGC CAC TCA GTG CCT GTC
```

```
       50                                             60
LYS SER CYS SER GLU PRO ARG CYS PHE ASN GLY GLY THR CYS GLN
AAA AGT TGC AGC GAG CCA AGG TGT TTC AAC GGG GGC ACC TGC CAG
```

```
                              70
GLN ALA LEU TYR PHE SER ASP PHE VAL CYS GLN CYS PRO GLU GLY
CAG GCC CTG TAC TTC TCA GAT TTC GTG TGC CAG TGC CCC GAA GGA
```

```
       80                                             90
PHE ALA GLY LYS CYS CYS GLU ILE ASP THR ARG ALA THR CYS TYR
TTT GCT GGG AAG TGC TGT GAA ATA GAT ACC AGG GCC ACG TGC TAC
```

```
                              100
GLU ASP GLN GLY ILE SER TYR ARG GLY THR TRP SER THR ALA GLU
GAG GAC CAG GGC ATC AGC TAC AGG GGC ACG TGG AGC ACA GCG GAG
```

```
       110                                            120
SER GLY ALA GLU CYS THR ASN TRP ASN SER SER ALA LEU ALA GLN
AGT GGC GCC GAG TGC ACC AAC TGG AAC AGC AGC GCG TTG GCC CAG
```

```
                              130
LYS PRO TYR SER GLY ARG ARG PRO ASP ALA ILE ARG LEU GLY LEU
AAG CCC TAC AGC GGG CGG AGG CCA GAC GCC ATC AGG CTG GGC CTG
```

```
       140                                            150
GLY ASN HIS ASN TYR CYS ARG ASN PRO ASP ARG ASP SER LYS PRO
GGG AAC CAC AAC TAC TGC AGA AAC CCA GAT CGA GAC TCA AAG CCC
```

```
                              160
TRP CYS TYR VAL PHE LYS ALA GLY LYS TYR SER SER GLU PHE CYS
TGG TGC TAC GTC TTT AAG GCG GGG AAG TAC AGC TCA GAG TTC TGC
```

```
       170                                            180
SER THR PRO ALA CYS SER GLU GLY ASN SER ASP CYS TYR PHE GLY
AGC ACC CCT GCC TGC TCT GAG GGA AAC AGT GAC TGC TAC TTT GGG
```

Fig. 5A.

```
                            190
ASN GLY SER ALA TYR ARG GLY THR HIS SER LEU THR GLU SER GLY
AAT GGG TCA GCC TAC CGT GGC ACG CAC AGC CTC ACC GAG TCG GGT 200                                     210
ALA SER CYS LEU PRO TRP ASN SER MET ILE LEU ILE GLY LYS VAL
GCC TCC TGC CTC CCG TGG AAT TCC ATG ATC CTG ATA GGC AAG GTT

220
TYR THR ALA GLN ASN PRO SER ALA GLN ALA LEU GLY LEU GLY LYS
TAC ACA GCA CAG AAC CCC AGT GCC CAG GCA CTG GGC CTG GGC AAA 230                             240
HIS ASN TYR CYS ARG ASN PRO ASP GLY ASP ALA LYS PRO TRP CYS
CAT AAT TAC TGC CGG AAT CCT GAT GGG GAT GCC AAG CCC TGG TGC

250
HIS VAL LEU LYS ASN ARG ARG LEU THR TRP GLU TYR CYS ASP VAL
CAC GTG CTG AAG AAC CGC AGG CTG ACG TGG GAG TAC TGT GAT GTG 260                                     270
PRO SER CYS SER THR CYS GLY LEU ARG GLN TYR SER GLN PRO GLN
CCC TCC TGC TCC ACC TGC GGC CTG AGA CAG TAC AGC CAG CCT CAG

280
PHE ARG ILE LYS GLY GLY LEU PHE ALA ASP ILE ALA SER HIS PRO
TTT CGC ATC AAA GGA GGG CTC TTC GCC GAC ATC GCC TCC CAC CCC 290                                     300
TRP GLN ALA ALA ILE PHE ALA LYS HIS ARG ARG SER PRO GLY GLU
TGG CAG GCT GCC ATC TTT GCC AAG CAC AGG AGG TCG CCC GGA GAG

310
ARG PHE LEU CYS GLY GLY ILE LEU ILE SER SER CYS TRP ILE LEU
CGG TTC CTG TGC GGG GGC ATA CTC ATC AGC TCC TGC TGG ATT CTC 320                                     330
SER ALA ALA HIS CYS PHE GLN GLU ARG PHE PRO PRO HIS HIS LEU
TCT GCC GCC CAC TGC TTC CAG GAG AGG TTT CCG CCC CAC CAC CTG

340
THR VAL ILE LEU GLY ARG THR TYR ARG VAL VAL PRO GLY GLU GLU
ACG GTG ATC TTG GGC AGA ACA TAC CGG GTG GTC CCT GGC GAG GAG 350                                     360
GLU GLN LYS PHE GLU VAL GLU LYS TYR ILE VAL HIS LYS GLU PHE
GAG CAG AAA TTT GAA GTC GAA AAA TAC ATT GTC CAT AAG GAA TTC

370
ASP ASP ASP THR TYR ASP ASN ASP ILE ALA LEU LEU GLN LEU LYS
GAT GAT GAC ACT TAC GAC AAT GAC ATT GCG CTG CTG CAG CTG AAA 380                                     390
SER ASP SER SER ARG CYS ALA GLN GLU SER SER VAL VAL ARG THR
TCG GAT TCG TCC CGC TGT GCC CAG GAG AGC AGC GTG GTC CGC ACT

400
VAL CYS LEU PRO PRO ALA ASP LEU GLN LEU PRO ASP TRP THR GLU
GTG TGC CTT CCC CCG GCG GAC CTG CAG CTG CCG GAC TGG ACG GAG 410                                     420
CYS GLU LEU SER GLY TYR GLY LYS HIS GLU ALA LEU SER PRO PHE
TGT GAG CTC TCC GGC TAC GGC AAG CAT GAG GCC TTG TCT CCT TTC
```

*Fig. 5B.*

```
                      430
TYR SER GLU ARG LEU LYS GLU ALA HIS VAL ARG LEU TYR PRO SER
TAT TCG GAG CGG CTG AAG GAG GCT CAT GTC AGA CTG TAC CCA TCC 440                                     450
SER ARG CYS THR SER GLN HIS LEU LEU ASN ARG THR VAL THR ASP
AGC CGC TGC ACA TCA CAA CAT TTA CTT AAC AGA ACA GTC ACC GAC

460
ASN MET LEU CYS ALA GLY ASP THR ARG SER GLY GLY PRO GLN ALA
AAC ATG CTG TGT GCT GGA GAC ACT CGG AGC GGC GGG CCC CAG GCA 470                                         480
ASN LEU HIS ASP ALA CYS GLN GLY ASP SER GLY GLY PRO LEU VAL
AAC TTG CAC GAC GCC TGC CAG GGC GAT TCG GGA GGC CCC CTG GTG

490
CYS LEU ASN ASP GLY ARG MET THR LEU VAL GLY ILE ILE SER TRP
TGT CTG AAC GAT GGC CGC ATG ACT TTG GTG GGC ATC ATC AGC TGG 500                                     510
GLY LEU GLY CYS GLY GLN LYS ASP VAL PRO GLY VAL TYR THR LYS
GGC CTG GGC TGT GGA CAG AAG GAT GTC CCG GGT GTG TAC ACC AAG 520                          527
VAL THR ASN TYR LEU ASP TRP ILE ARG ASP ASN MET ARG PRO OP
GTT ACC AAC TAC CTA GAC TGG ATT CGT GAC AAC ATG CGA CCG TGA
```

CCAGGAACACCCGACTCCTCAAAAGCAAATGAGATCCCGCCTCTTCTTCTTCAGAAGACA

CTGCAAAGGCGCAGTGCTTCTCTACAGACTTCTCCAGACCCACCACACCGCAGAAGCGGG

ACGAGACCCTACAGGAGAGGGAAGAGTGCATTTTCCCAGATACTTCCCATTTTGGAAGT

TTTCAGGACTTGGTCTGATTTCAGGATACTCTGTCAGATGGGAAGACATGAATGCACACT

AGCCTCTCCAGGAATGCCTCCTCCCTGGGCAGAAAGTGGCCATGCCACCCTGTTTTCAGCTA

AAGCCCAACCTCCTGACCTGTCACCGTGAGCAGCTTTGGAAACAGGACCACAAAAATGAA

AGCATGTCTCAATAGTAAAAGATAACAAGATCTTTCAGGAAAGACGGATTGCATTAGAA

ATAGACAGTATATTTATAGTCACAAGAGCCCAGCAGGGCCTCAAAGTTGGGGCAGGCTGGC

TGGCCCGTCATGTTCCTCAAAAGCACCCTTGACGTCAAGTCTCCTTCCCCTTTCCCCACT

CCCTGGCTCTCAGAAGGTATTCCTTTTGTGTACAGTGTGTAAAGTGTAAATCCTTTTTCT

TTATAAACTTTAGAGTAGCATGAGAGAATTGTATCATTTGAACAACTAGGCTTCAGCATA

TTTATAGCAATCCATGTTAGTTTTTACTTTCTGTTGCCACAACCCTGTTTTATACTGTA

CTTAATAAATTCAGATATATTTTTCACAGTTTTTCCAAAAAAAAAAAAAA

*Fig. 5C.*

METHOD OF TREATMENT USING RECOMBINANT HUMAN TISSUE PLASMINOGEN ACTIVATOR

This is a continuation of application Ser. No. 08/487,456, filed Jun. 6, 1995, now U.S. Pat No. 5,869,314; which is a continuation of application Ser. No. 08/264,134, filed Jun. 21, 1994, now U.S. Pat. No. 5,587,159; which is a continuation of application Ser. No. 08/109,698 filed Aug. 20, 1993, now abandoned; which is a continuation of application Ser. No. 07/911,021 filed Jul. 9, 1992, now abandoned; which is a continuation of application Ser. No. 07/489,855 filed Mar. 2, 1990, now U.S. Pat. No. 5,185,259; which is a continuation of application Ser. No. 07/012,694, filed Feb. 9, 1987, now abandoned; which is a division of application Ser. No. 06/483,052 filed Apr. 7, 1983, now U.S. Pat. No. 4,766,075; as is application Ser. No. 07/184,477 filed Apr. 21, 1988, now U.S. Pat. No. 4,853,330; which is a division of application Ser. No. 06/483,052 filed Apr. 7, 1983, now U.S. Pat. No. 4,766,075; which is a continuation-in-part of application Ser. No. 06/398,003, filed Jul. 14, 1982, now abandoned, and of application Ser. No. 06/374,860, filed May 5, 1982, now abandoned.

This is a continuation-in part of application Ser. Nos. 398,003 filed Jul. 14, 1982 and 374,860, filed May 5 1982.

FIELD OF THE INVENTION

The present invention relates to human plasminogen activator, corresponding to that found in human serum and/or tissues, and to novel forms and compositions thereof and particularly to the means and methods for its production to homogeneity in therapeutically significant quantities.

The present invention arises in part from the discovery of the DNA sequence and deduced amino acid sequence of human plasminogen activator. This discovery enabled the production of human plasminogen activator via the application of recombinant DNA technology, in turn, enabling the production of sufficient quality and quantity of material to initiate and conduct animal and clinical testing as prerequisites to Market approval, unimpeded by the restrictions necessarily inherent in the isolation methods hitherto employed involving production and extraction from existing cell culture. This invention is directed to these associated embodiments in all respects.

The publications and other materials hereof used to illuminate the background of the invention, and in particular cases, to provide additional details concerning its practice are incorporated herein by reference, and for convenience, are numerically referenced in the following text and respectively grouped in the appended bibliography.

BACKGROUND OF THE INVENTION

A. Human Tissue Plasminogen Activator

The fibrinolytic system is in a dynamic equilibrium with the coagulation system, maintaining an intact, patent vascular bed. The coagulation system deposits fibrin as a matrix serving to restore a hemostatic condition. The fibrinolytic system removes the fibrin network after the hemostatic condition is achieved. The fibrinolytic process is brought about by the proteolytic enzyme plasmin that is generated from a plasma protein precursor plasminogen. Plasminogen is converted to plasmin through activation by an activator.

Currently, two activators are commercially available, streptokinase and urokinase. Both are indicated for the treatment of acute vascular diseases such as myocardial infarct, stroke, pulmonary embolism, deep vein thrombosis, peripheral arterial occlusion and other venous thromboses. Collectively, these diseases account for major health hazards and risks.

The underlying etiological basis for these diseases points to either a partial, or in severe cases, total occlusion of a blood vessel by a blood clot—thrombus or thromboembolus. Traditional anticoagulant therapy, as with heparin and coumarin, does nothing to directly enhance dissolution of thrombi or thromdoemboli. The thrombolytic agents referred to earlier, streptokinase and urokinase have enjoyed practical and effective use. However, each has severe limitations. Neither has a high affinity for fibrin; consequently both activate circulating and fibrin-bound plasminogen relatively indiscriminately. The plasmin formed in circulating blood is neutralized rather quickly and lost for useful thrombolysis. Residual plasmin will degrade several clotting factor proteins, for example, fibrinogen, Factor V and Factor VIII, causing a hemorrhagic potential. In addition, streptokinase is strongly antigenic and patients with high antibody titers respond inefficiently to treatment and cannot remain on continuous treatment. Urokinase therapy is expensive, owing to its involved isolation from human urine or tissue culture, and it, therefore, is not generally accepted in clinical practice. Urokinase has been the subject of numerous investigations—See, for example, references 1–6.

So-called plasminogen activators have been isolated from various human tissue, e.g.,, uterine tissue, blood, serum—see generally references 7–11 and from cell culture (reference 94). Compositions thereof have also been described—see references 12, 13. See also references 14–18. The plasminogen activators derived from these sources have been classified into two major groups: urokinase-type plasminogen activators (u-PA) and tissue-type plasminogen activators (t-PA) based on differences in their immunological properties. (The abbreviations t-PA and u-PA are those proposed at the XXVIII Meeting of the International Committee on Thrombosis and Hemostasis, Bergamo, Italy, Jul. 27, 1982.)

Recently, a human melanoma line has been identified which secretes t-PA. Characterization of this melanoma plasminogen activator has shown it to be indistinguishable both immunologically and in amino acid composition from the plasminogen activator isolated from normal human tissue (Reference 19, 88).

The product was isolated in relatively pure form, characterized and found to be a highly active fibrinolytic agent (20).

Several studies (eq. References 95 to 98) which used t-PA purified from the melanoma cell line have demonstrated its higher affinity for fibrin, compared with urokinase type plasminogen activators. More intensive investigation of human t-PA as a potential thrombolytic agent has, however, been hampered by its extremely low concentration in blood, tissue extracts, vessel perfusates and cell cultures.

It was perceived that the application of recombinant DNA and associated technologies would be a most effective way of providing the requisite large quantities of high quality human tissue-type plasminogen activator (earlier referred to as human plasminogen activator), essentially free of other human protein. Such materials would probably exhibit bioactivity admitting of their use clinically in the treatment of various cardiovascular conditions or diseases.

B. Recombinant DNA Technology

Recombinant DNA technology has reached the age of some sophistication. Molecular biologists are able to recombine various DNA sequences with some facility, creating new DNA entities capable of producing copious amounts of exogenous protein product in transformed microbes and cell cultures. The general means and methods are in hand for the in vitro ligation of various blunt ended or "sticky" ended fragments of DNA, producing potent expression vehicles useful in transforming particular organisms, thus directing their efficient synthesis of desired exogenous product. However, on an individual product basis, the pathway remains somewhat tortuous and the science has not advanced to a stage where regular predictions of success can be made. Indeed, those who portend successful results without t he underlying experimental basis, do so with considerable risk of inoperability.

DNA recombination of the essential elements, i.e. an origin of replication, one or more phenotypic selection characteristics, an expression promoter, heterologous gene insert and remaining vector, generally is performed outside the host cell. The resulting recombinant replicable expression vehicle, or plasmid, is introduced into cells by transformation and large quantities of the recombinant vehicle obtained by growing the transformant. Where the gene is properly inserted with reference to portions which govern the transcription and translation of the encoded DNA message, the resulting expression vehicle is useful to actually produce the polypeptide sequence for which the inserted gene codes, a process referred to as expression. The resulting product may be obtained by lysing, if necessary, the host cell, in microbial systems, and recovering the product by appropriate purification from other proteins.

In practice, through the use of recombinant DNA technology, one can express entirely heterologous polypeptides—so-called direct expression—or alternatively may express a heterologous polypeptide fused to a portion of the amino acid sequence of a homologous polypeptide. In the latter cases, the intended bioactive product is sometimes rendered bioinactive within the fused homologous/ heterologous polypeptide until it is cleaved in an extracellular environment. See references (21) and (22).

Similarly, the art of cell or tissue cultures for studying genetics and cell physiology is well established. Means and methods are in hand for maintaining permanent cell lines, prepared by successive serial transfers from isolate normal cells. For use in research, such cell lines are maintained on a solid support in liquid medium, or by growth in suspension containing support nutriments. Scale-up for large preparations seems to pose only mechanical problems. For further background, attention is directed to references (23) and (24).

Likewise, protein biochemistry is a useful, indeed necessary, adjunct in biotechnology. Cells producing the desired protein also produce hundreds of other proteins, endogenous products of the cell's metabolism. These contaminating proteins, as well as other compounds, if not removed from the desired protein, could prove toxic if administered to an animal or human in the course of therapeutic treatment with desired protein. Hence, the techniques of protein biochemistry come to bear, allowing the design of separation procedures suitable for the particular system under consideration and providing a homogeneous product safe for intended use. Protein biochemistry also proves the identity of the desired product, characterizing it and ensuring that the cells have produced it faithfully with no alterations or mutations. This branch of science is also involved in the design of bioassays, stability studies and other procedures necessary to apply before successful clinical studies and marketing can take place.

SUMMARY OF THE INVENTION

The present invention is based upon the discovery that recombinant DNA technology can be used successfully to produce human tissue plasminogen activator (t-PA), preferably in direct form, and in amounts sufficient to initiate and conduct animal and clinical testing as prerequisites to market approval. The product human t-PA it suitable for use, in all of its forms, in the prophylactic or therapeutic treatment of human beings for various cardiovascular conditions or diseases. Accordingly, the present invention, in one important aspect, is directed to methods of treating vascular disorders in human subjects using t-PA and to suitable pharmaceutical compositions thereof.

The present invention further comprises essentially pure human tissue plasminogen activator. The product produced by genetically engineered microorganisms or cell culture systems provides an opportunity to produce human tissue Plasminogen activator in a much more efficient manner than has been possible, enabling hitherto elusive commercial exploitation, In addition, depending upon the host cell, the human tissue plasminogen activator hereof may contain associated glycosylation to a greater or lesser extent compared with native material. In any event, the t-PA will be free of the contaminants normally associated with it in its non-recombinant cellular environment.

The present invention is also directed to replicable DNA expression vehicles harboring gene sequences encoding human tissue plasminogen activator in expressible form, to microorganism strains or cell cultures transformed with them and to microbial or cell cultures of such transformed strains or cultures, capable of producing human tissue plasminogen activator. In still further aspects, the present invention is directed to various processes useful for preparing said gene sequences, DNA expression vehicles, microorganism strains and cell cultures, and specific embodiments thereof. Still further, this invention is directed to the preparation of fermentation cultures of said microorganisms and cell cultures.

BRIEF DESCRIPTION OF THE DRAWINGS

FIGS. 5a, 5b, and 5c show the nucleotide sequence and deduced amino acid sequence of the full length human t-PA cDNA.

DETAILED DESCRIPTION

A. Definitions

Figure 1:
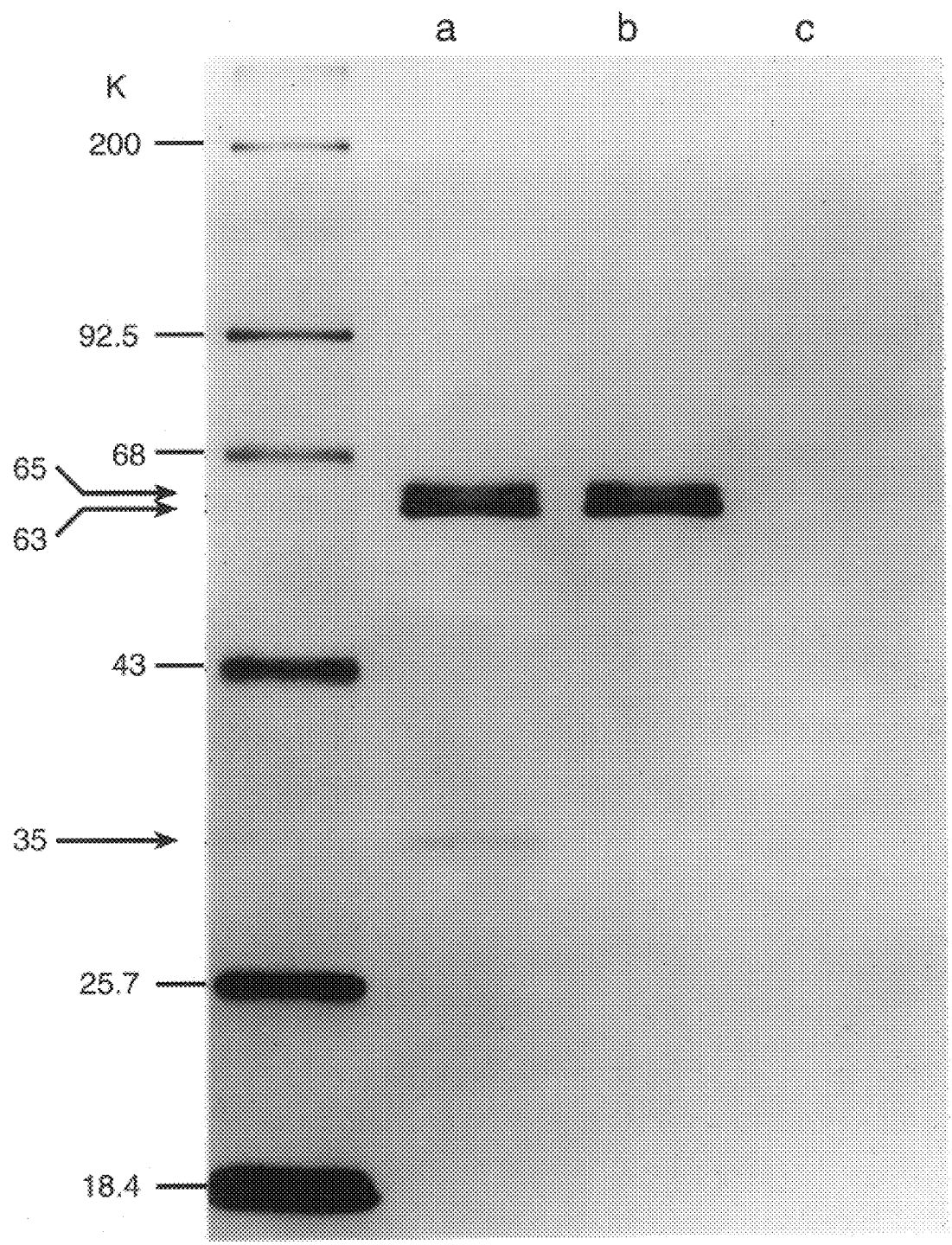
FIG. 1 shows a 10% sodium dodecylsulfate polyacrylamide gel electrophoresis (SDS PAGE) of $35_s$-methionine labelled proteins precipitable with anti t-PA IgG secreted from melanoma cells with and without protease inhibitor.

As used herein, "human tissue plasminogen activator" or "human t-PA" or "t-PA" denotes human extrinsic (tissue-type) plasminogen activator produced by microbial or cell culture systems, in bioactive forms comprising a protease portion and corresponding to those tissue plasminogen activators otherwise native to human tissue. The human tissue plasminogen activator protein produced herein has been defined by means of determined DNA gene and deductive amino acid sequencing. It will be understood that natural allelic variations exist and occur from individual to individual. These variations may be demonstrated by (an) amino acid differences) in the overall sequence or by deletions, substitutions, insertions, inversions or additions of (an) amino acid(s) in said sequence. In addition, the location of and degree of glycosylation will depend on the nature of the host cellular environment.

The potential exists, in the use of recombinant DNA technology, for the preparation of various human tissue plasminogen activator derivatives, variously modified by resultant single or multiple amino acid substitutions, deletions, additions or replacements, for example, by means of site directed mutagenesis of the underlying DNA. Included would be the preparation of derivatives retaining the essential kringle region and serine protease region characteristic generally of the human tissue plasminogen activator described specifically herein, but otherwise modified as described above. All such allelic variations and modifications resulting in derivatives of human tissue plasminogen activator are included within the scope of this invention, as well as other related human extrinsic (tissue-type) plasminogen activators, similar physically and biologically, so long as the essential, characteristic human tissue plasminogen activator activity remains unaffected in kind.

Human tissue plasminogen activator is prepared 1) having methionine as its first amino acid (present by virtue of the ATG start signal codon insertion in front of the structural gene) or 2) where the methionine is intra- or extracellularly cleaved, having its normally first amino acid, or 3) together with either its signal polypeptide or a conjugated protein other than the conventional signal polypoptide, the signal polypeptide or conjugate being specifically cleavable in an intra- or extracellular environment (See reference 21), or 4) by direct expression in mature form without the necessity of cleaving away any extraneous, superfluous polypeptide. The latter is particularly important where a given host may not, or not efficiently, remove a signal peptide where the expression vehicle is designed to express the tissue plasminogen activator together with its signal peptide. In any event, the thus produced human t-PA, in its various forms, is recovered and purified to a level fitting it for use in the treatment of various vascular conditions or diseases.

Furthermore, t-PA has forms which include both the single chain (1-chain) protein and the 2-chain protein. The latter is proteolytically derived from the 1-chain compound. It is theorized that the 2-chain protein is associated with produced fibrin and that proteolytic conversion from 1- to 2-chain material occurs at the locus of the conversion of plasminogen to plasmin. The present invention provides for the administration of the 1-chain protein for in vivo conversion as just described for the administration of 2-chain protein, which has also been shown to be active. The 2-chain protein can be prepared by in vitro proteolytic conversion after the 1-chain material is produced. A so-called "kringle" area is positioned upstream from the serine protease portion and is believed to play an important function in binding the tissue plasminogen activator hereof to a fibrin matrix; hence, the observed specific activity of the present tissue lasminogen activator toward tangible, extant thrombi. The tissue plasminogen activator hereof is produced containing the enzymatically active portion corresponding to native material and the term human tissue plasminogen activator defines products comprising such portion alone or together with additional amino acid sequences up to the full length molecule.

To summarize in the present invention, human t-PA thus has a functional definition; it is capable of catalyzing the conversion of plasminogen to plasmin, binds to fibrin, and is classified as a t-PA based on immunological properties as set forth hereinabove.

"Essentially pure form" when used to describe the state of human t-PA produced by the invention means free of protein or other materials normally associated with human t-PA when produced by non-recombinant cells, i.e. in its "native" environment.

"DHFR protein" refers to a protein which is capable of the activity associated with dihydrofolate reductase (DHFR) and which, therefore, is required to be produced by cells which are capable of survival on medium deficient in hypoxanthine, glycine, and thymidine (-HGT medium). In general, cells lacking DHFR protein are incapable of growing on this medium, cells which contain DHFR protein are successful in doing so.

"Cells sensitive to MTX" refers to cells which are incapable of growing on media which contain the DHFR inhibitor methotrexate (MTX). Thus, "cells sensitive to MTX" are cells which, unless genetically altered or otherwise supplemented, will fail to grow under ambient and medium conditions suitable for the cell type when the MTX concentration is 0.2 $\mu$g/ml or more. Some cells, such as bacteria, fail to exhibit MTX sensitivity due to their failure to permit MTX inside their cell boundaries, even though they contain DHFR which would otherwise be sensitive to this drug. In general, cells which contain, as their. DHFR protein, wild type DHFR will be sensitive to methotrexate if they are permeable or capable of uptake with respect to MTX.

"Wild type DHFR" refers to dihydrofolate reductase as is ordinarily found in the particular organism in question. Wild type DHFR is generally sensitive in vitro to low concentrations of methotrexate.

"DHFR protein with low binding affinity for MTX" has a functional definition. This is a DHFR protein which, when generated within cells, will permit the growth of MTX sensitive cells in a medium containing 0.2 $\mu$g/ml or more of MTX. It is recognized that such a functional definition depends on the facility with which the organism produces the "DHFR protein with low binding affinity for MTX" as well as upon the protein itself. However, as used in the context of this invention, such a balance between these two mechanisms should not be troublesome. The invention operates with respect to conferring the capability of surviving these levels of MTX, and it is not consequential whether the ability to do so is impacted by increased expression in addition to the innate nature of the DHFR produced. A convenient DHFR protein which fits this definition is disclosed in U.S. application Ser. No. 459,151, filed Jan. 19, 1983, incorporated herein by reference.

"Expression vector" includes vectors which are capable of expressing DNA sequences contained therein, where such sequences are operably linked to other sequences capable of effecting their expression. It is implied, although not always explicitly stated, that these expression vectors must be replicable in the host organisms either as episomes or as an integral part of the chromosomal DNA. Clearly a lack of replicability would render them effectively inoperable. In sum, "expression vector" is given a functional definition, and any DNA sequence which is capable of effecting expression of a specified DNA code disposed therein is included in this term a it is applied to the specified sequence. In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

"Recombinant host cells" refers to cells which have been transformed with vectors constructed using recombinant DNA techniques. As defined herein, t-PA Is produced in the amounts achieved by virtue of this transformation, rather than in such lesser amounts, or, more commonly, in such less than detectable amounts, as might be produced by the untransformed host. t-PA produced by such cells can be referred to as "recombinant t-PA".

B. Host Cell Cultures and Vectors

The vectors and methods disclosed herein are suitable for use in host cells over a wide range of prokaryotic and eukaryotic organisms.

In general, of course, prokaryotes are preferred for cloning of DNA sequences in constructing the vectors useful in the invention. For example, E. coli K12 strain 294 (ATCC No. 31446) is particularly useful. Other microbial strains which may be used include E. coli strains such as E. coli B, and E. coli. X1776 (ATCC No. 31537). These examples are, of course, intended to be illustrative rather than limiting.

Prokaryotes may also be used for expression. The aforementioned strains, as well as E. coli W3110 (F⁻, λ⁻, prototrophic, ATCC No. 27325), bacilli such as Bacillus subtilus, and other enterobacteriaceae such as Salmonella typhimurium, or Serratia marcescons, and various pseudemonas species may be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species (Bolivar, et al., Gene 2: 95 (1977)). pBR322 contains genes for ampicillin and tetracycline resistance and thus provides easy means for identifying transformed cells. The pBR322 plasmid, or other microbial plasmid must also contain, or be modified to contain, promoters which can be used by the microbial organism for expression of its own proteins. Those promoters most commonly used in recombinant DNA construction include the β-lactamase (penicillinase) and lactose promoter systems (Chang et al, Nature, 275: 617 (1978); Itakura, et al, Science, 198: 1056 (1977); (Goeddel, et al Nature 281: 544 (1979)) and a tryptophan (trp) promoter system (Goeddel, et al, Nucleic Acids Res., 8: 4057 (1980); EPO Appl Publ No. 0036776). While these are the most commonly used, other microbial promoters have been discovered and utilized, and details concerning their nucleotide sequences have been published, enabling a skilled worker to ligate them functionally with plasmid vectors (Siebenlist, et al, Cell 20: 269 (1980)).

In addition to prokaryotes, eukaryotic microbes, such as yeast cultures may also be used. Saccharomyces cerevisiae, or common baker's yeast is most commonly used among eukaryotic microorganisms, although a number of other strains are commonly available. For expression in Saccharomyces, the plasmid YRp7, for example, (Stinchcomb, et al, Nature, 282: 39 (1979); Kingsman et al, Gene, 7: 141 (1979); Tschemper, et al, Gene, 10: 157 (1980)) is commonly used. This plasmid already contains the trp1 gene which provides a selection marker for a mutant strain of yeast lacking the ability to grow in tryptophan, for example ATCC No. 44076 or PEP4-1 (Jones, Genetics, 85: 12 (1977)). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman, et al., J. Biol. Chem., 255: 12073 (1980)) or other glycolytic enzymes (Hess, et al, J. Adv. Enzyme Reg., 7: 149 (1968); Holland, et al, Biochemistry, 17: 4900 (1978)), such as enolase, glyceraldehyde-3-phosphate dehydrogenase, hexokinase, pyruvate decarboxylase, phosphofructokinase, glucose-6-phosphate, isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter regions for alcohol dehydrogenase 2, isoctochrome C, acid phosphatase, degradative enzymes associated with nitrogen metabolism, and the aforementioned glyceraldehyde-3-phosphate dehydrogenase, and enzymes responsible for maltose and galactose utilization (Holland, ibid.). Any plasmid vector containing yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However interest has been greatest in vertebrate cells, and propogation of vertebrate cells in culture (tissue culture) has become a routing procedure in recent years [Tissue Culture, Academic Press, Kruse and Patterson, editors (1973)]. Examples of such useful host cell lines are VERO and HeLa cells, Chinese hamster ovary (CHO) cell lines, and W138, BHK, COS-7 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers, et al, *Nature,* 273: 113 ((1978) incorporated herein by reference. Smaller or larger SV40 fragments may also be used, provided there is included the approximately 250 bp sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g. Polyoma, Adeno, VSV, BPV, etc.) source, or may be provided by the host cell chromosomal replication mechanism. If the vector is integrated into the host cell chromosome, the latter is often sufficient.

In selecting a preferred host cell for transfection by the vectors of the invention which comprise DNA sequences encoding both t-PA and DHFR protein, it is appropriate to select the host according to the type of DHFR protein employed. If wild type DHFR protein is employed, it is preferable to select a host cell which is deficient in DHFR, thus permitting the use of the DHFR coding sequence as a marker for successful transfection in selective medium which lacks hypoxyanthine, glycine, and thymidine. An appropriate host cell in this case is the Chinese hamster ovary (CHO) cell line deficient in DHFR activity, prepared and propagated as described by Urlaub and Chasin, *Proc. Natl. Acad. Sci. (USA)* 77: 4216 (1980), incorporated herein by reference.

On the other hand, if DHFR protein with low binding affinity for MTX is used as the controlling sequence, it is not necessary to use DHFR deficient cells. Because the mutant DHFR is resistant to methotrexate, MTX containing media can be used as a means of selection provided that the host cells are themselves methotrexate sensitive. Most eukaryotic cells which are capable of absorbing MTX appear to be methotrexate sensitive. One such useful cell line is a CHO line, CHO-K1 ATCC No. CCL 61.

Examples which are set forth hereinbelow describe use of *E. coli* using the lac and trp promoter system and use of CHO cells as host cells, and expression vectors which include the SV40 origin of replication as a promoter. However, it would be well within the skill of the art to use analogous techniques to construct expression vectors for expression of desired protein sequences in alternative prokaryotic or eukaryotic host cell cultures.

Satisfactory amounts of human t-PA are produced by cell cultures, however, later refinements using a secondary coding sequence serve to enhance production levels even further. The secondary coding sequence serve to enhance production levels even further. The secondary coding sequence comprises dehydrofolate reductase (DHFR) which is affected by an externally controlled parameter, such as methotrexate, thus permitting control of expression by control of the methotrexate (MTX) concentration.

C. Methods Employed

If cells without formidable cell membrane barriers are used as host cells, transfection is carried out by the calcium phosphate precipitation method as described by Graham and Van der Eb, *Virology,* 52: 456 (1973). However, other methods for introducing DNA into cells such as by nuclear injection or by protoplast fusion may also be used.

If prokaryotic cells or cells which contain substantial cell wall constructions are used, the preferred method of transfection is calcium treatment using calcium chloride as described by Cohen, F. N. et al *Proc. Natl. Acad. Sci. (USA),* 69: 2110 (1972).

Construction of suitable vectors containing the desired coding and control sequences employ standard ligation techniques. Isolated plasmids or DNA fragments are cleaved, tailored, and religated in the form desired to form the plasmids required.

Cleavage is performed by treating with restriction enzyme (or enzymes) in suitable buffer. In general, about 1 μg plasmid or DNA fragments is used with about 1 unit of enzyme in about 20 μl of buffer solution. (Appropriate buffers and substrate amounts for particular restriction enzymes are specified by the manufacturer.) Incubation times of about 1 hour at 37° C. are workable. After incubations, protein is removed by extraction with phenol and chloroform, and the nucleic acid is recovered for the aqueous fraction by precipitation with ethanol.

If blunt ends are required, the preparation is treated for 15 minutes at 15° C. with 10 units of Polymerase I (Klenow), phenol-chloroform extracted, and ethanol precipitated.

Size separation of the cleaved fragments is performed using 6 percent polyacrylamide gel described by Goeddel, D., et al, *Nucleic Acids Res.,* 8: 4057 (1980) incorporated herein by reference.

For litigation approximately equimolar amounts of the desired components, suitably end tailored to provide correct matching are treated with about 10 units T4 DNA ligase per 0.5 μg DNA. (When cleaved vectors are used as components, it may be useful to prevent religation of the cleaved vector by pretreatment with bacterial alkaline phosphatase.)

For analysis to confirm correct sequences in plasmids constructed, the litigation mixtures are used to transform *E. coli* K12 strain 294 (ATCC 31446), and successful transformants selected by ampicillin or tetracycline resistance where appropriate. Plasmids from the transformants are prepared, analyzed by restriction and/or sequenced by the method of Messing, et al, *Nucleic Acids Res.,* 9:309 (1981) or by the method of Maxam, et al, *Methods in Enzymology,* 65:499 (1980).

Amplification of DHFR protein coding sequences is effected by growing host cell cultures in the presence of approximately 20–500,000 nM concentrations of methotrexate, a competitive inhibitor of DHFR activity. The effective range of concentration is highly dependent, of course, upon the nature of the DHFR gene, protein and the characteristics of the host. Clearly, generally defined upper and lower limits cannot be ascertained. Suitable concentrations or other folic acid analogs or other compounds which inhibit DHFR could also be used. MTX itself is, however, convenient, readily available and effective.

D. General Description of Preferred Embodiments

Human tissue plasminogen activator was obtained according to the following protocol:

1. Human melanoma cells actively producing tissue plasminogen activator were cultured to confluency.
2. Cell pellets from such cell cultures were extracted in the presence of ribonuclease inhibitors to isolate all cytoplasmic RNA.
3. An oligo-dT column isolated the total messenger RNA (mRNA) in polyadenylated form. This mRNA was size fractionated using acid-urea agarose gel electrophoresis.

4. The gel fraction containing tissue plasminogen activator specific RNA was identified in the following manner: The RNA from each of the gel fractions was translated in a rabbit reticulocyte lysate in vitro system supplemented with dog pancreas microsomes. The resulting translation products were then immunoprecipitated with human tissue plasminogen activator specific IgG antibody.

5. The appropriate RNA (21 to 24S) was converted to corresponding single stranded complementary DNA (cDNA) from which was produced double stranded cDNA. After poly-dC tailing, it was inserted into a vector, such as a plasmid bearing one or more phenotypic markers.

6. The thus prepared vectors were used to transform bacterial cells providing a cloned cDNA library. A pool of radiolabeled synthetic deoxy oligonucleotides complementary to codons for known amino acid sequences in t-PA, such as, for example the pool of 8 14-mers,

(complementary to sequences coding for the known—see infra—amino acid sequence: tryptophan—glutamic acid—tyrosine—cysteine—aspartic acid (W-E-Y-C-D) was prepared and used to probe the colony library.

7. From the positive cDNA clones plasmid DNA was isolated and sequenced.

8. The sequenced DNA encoding t-PA was then tailored in vitro for insertion into an appropriate expression vehicle which was used to transform an appropriate host cell, which was, in turn, permitted to grow in a culture and to produce the desired human tissue plasminogen activator.

9. Human tissue plasminogen activator thus produced has ca. 251 amino acids in its enzymatic serine protease portion and a "kringle" containing sequence upstream therefrom which is presently believed to be responsible for fibrin binding. The mature protein plus its signal presequence, totals 562 amino acids.

The foregoing procedure, in itself, is successful in producing pure t-PA. Methods of the invention employing an additional coding sequence sensitive to methotrexate permit the production in host cell cultures of antigenically active t-PA protein in amounts greater than 0.1 pg per cell per day. With suitable application of amplifying conditions, amounts greater than 20 pg per cell per day can be obtained. Stated in alternative terms, gene expression levels resulting in production of more than $9 \times 10^{-6}$ Plough units per cell per day, or, with suitable amplification, more than $18 \times 10^{-4}$ Plough units of t-PA activity are achieved.

Advantage is taken in this aspect of the invention of methotrexate as a drug which, while normally fatal to cells capable of its uptake, permits cells to grow in the presence of controlled levels of MTX by amplification of the gene coding for the DHFR coding sequence (Schimke, Robert T. et al, *Science,* 202: 1051 (1978); Biedler, J. L. et al, *Cancer Res.* 32: 153 (1972); Chang, S. E. et al, *Cell,* 7: 391 (1976)).

Of importance to this aspect of the invention is the showing that amplification of the gene for DHFR may cause amplification of associated sequences which code for other proteins. This appears to be the case when the associated protein is hepatitis B surface antigen (HBsAg) (Christman, J. et al, *Proc. Natl. Acad. Sci.,* 79: 1815 (1982)); the *E. coli* protein XGPRT (Ringold, Gordon, et al, *J. Molec. and Appl. Gen.,* 1: 165 (1981)); and an endogenous sequence for a DHFR/SV40 plasmid combination (Kaufman, R. F. et al, *J. Molec. Biol.,* 159: 601 (1982).

Other mechanisms for conferring methotrexate resistance include diminution of the binding affinity of the DHFR protein, so that it is less susceptible to methotrexate (Flintoff, W. F. et al, *Somat. Cell Genet.,* 2: 245 (1976)) but in this instance, amplification appears to occur as well.

It would appear that the genes both for wild type DHFR and for DHFR which is resistant to MTX by virtue of its own decreased binding capacity are amplified by the presence of MTX. Hence, jn principle, this aspect of the invention herein concerns using the impact of DHFR sequence amplification on associated protein coding sequences to provide a control mechanism which permits enhanced expression levels of t-PA sequences in the presence of MTX, or by virtue of prior treatment of transformed cells with MTX.

E. Examples

The following examples are intended to illustrate but not to limit the invention. In the examples here an *E. coli* host culture and a CHO cell line suitable for the type of DHFR protein coding sequence to be introduced were employed as host cell cultures. However, other eukaryotic and prokaryotic cells are suitable for the method of the invention as well.

E.1 Expression of the Human t-PA Gene in *E. coli*
E.1.A Figure Legends

FIG. 1 is an autoradiogram of a 10 percent SDS RAGE displaying the immunoprecipitated [$^{35}$S]-methionine labeled protein(s) secreted from human melanoma cells during a 3 hour pulse in vivo, in the presence (lane b) or absence (lane a) of the protease inhibitor aprotinin. After immunoprecipitation with tissue plasminogen activator specific IgG, three bands were observed (lane a) having molecular weights of approximately 65,000, 63,000 and 35,000. In the presence of the protease inhibitor, however, no 35,000 molecular weight species is observed. No products are immunoprecipitated when preimmune serum is used (lane c). The migrations and molecular weights of $^{14}$C- labelled protein standards are shown to the left of lane a.

Figure 2:
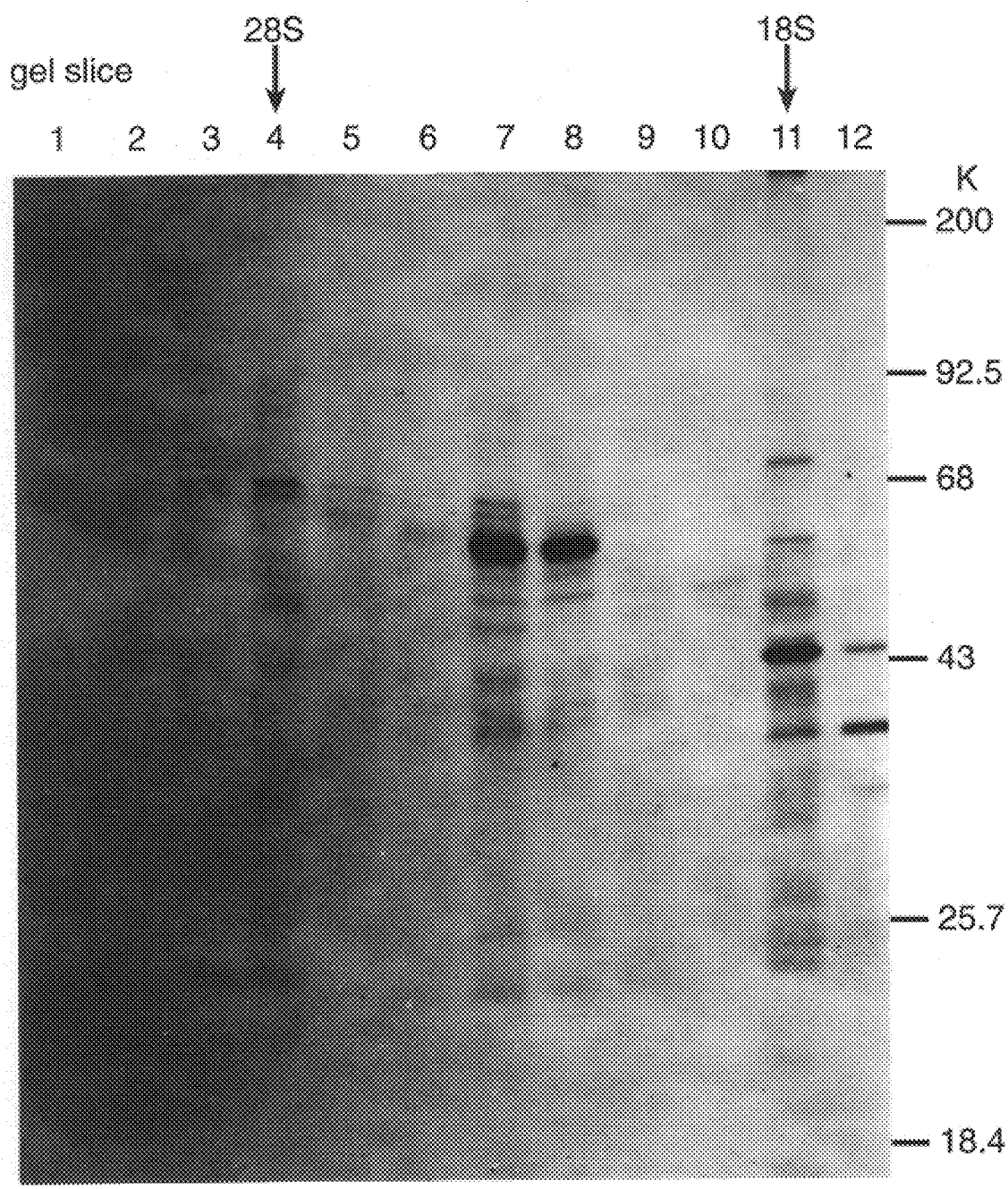
FIG. 2 shows electropheresis of the immunoprecipitated translation products of mRNA fractions derived from melanoma cells.

FIG. 2 depicts the gel electrophoresis of the immunoprecipitated translation products of RNA fractions isolated from an acid urea agarose gel. A major band was observed in fraction numbers 7 and 8 after translation in the presence of dog pancreas microsomes followed by immune precipitation with tissue plasminogen activator specific IgG. This band has a molecular weight of approximately 63,000 daltons. The size of the mRNA migrating in fractions 7 and 8 is approximately 21 to 24S. The positions of ribosomal RNA markers which were determined after electrophoresis on the RNA urea gel and visualized by ethidium bromide staining are labeled above the appropriate gel lanes.

Figure 3:
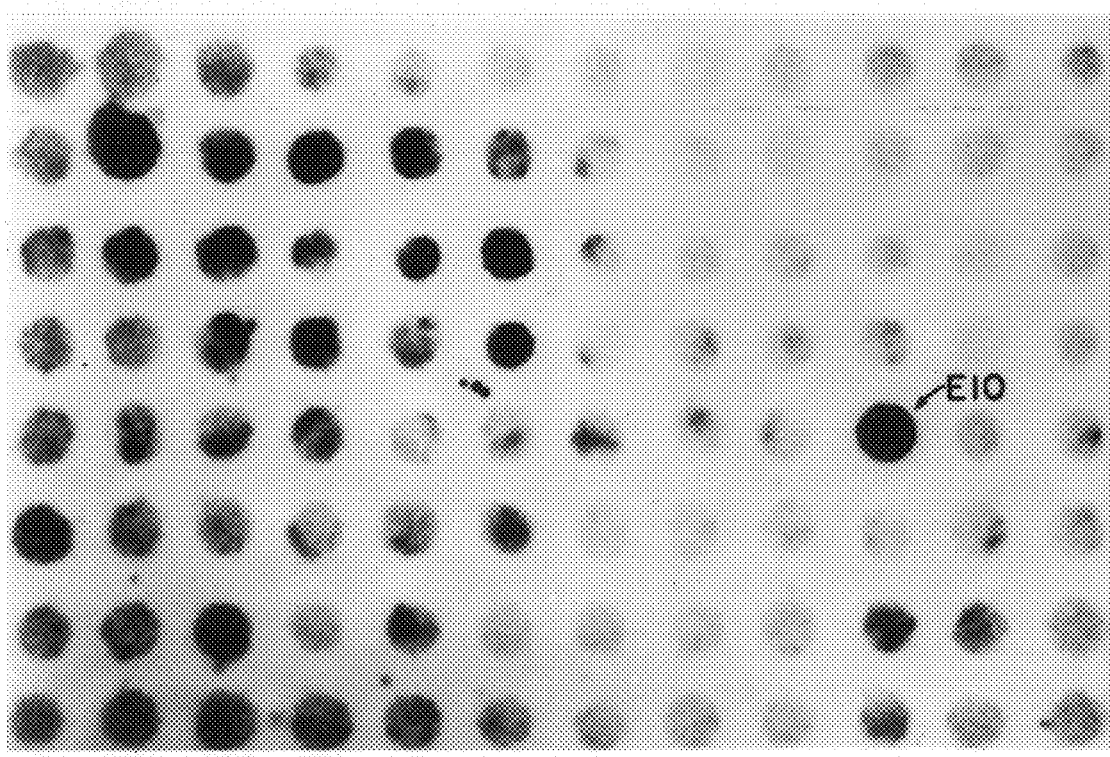
FIG. 3 shows the hybridization pattern of 96 bacterial transformed with cDNA using the pool of $^{32}P$ labeled 14-mer as probe prepared based on a 5 amino acid sequence of human t-PA.

FIG. 3 displays the hybridization pattern of 96 colonies with

(W-E-Y-C-D) probe. 96 individual transformants were grown in a microtiter plate, replica plated and grown on a nitrocellulose membrane. The colonies were the lysed, bacterial DNA fixed and the filters were hybridized with the $^{32}$P-14-mer (W-E-Y-C-D) probes. The filters were washed to remove nonhybridized probe and exposed to X-ray film. This autoradiogram is representative of the patterns obtained with 48 individual filters (4 600 independent colonies). An example of a positive tissue plasminogen activator cDNA clone on filter number 25 is labelled as E10 (arrow).

Figure 4:
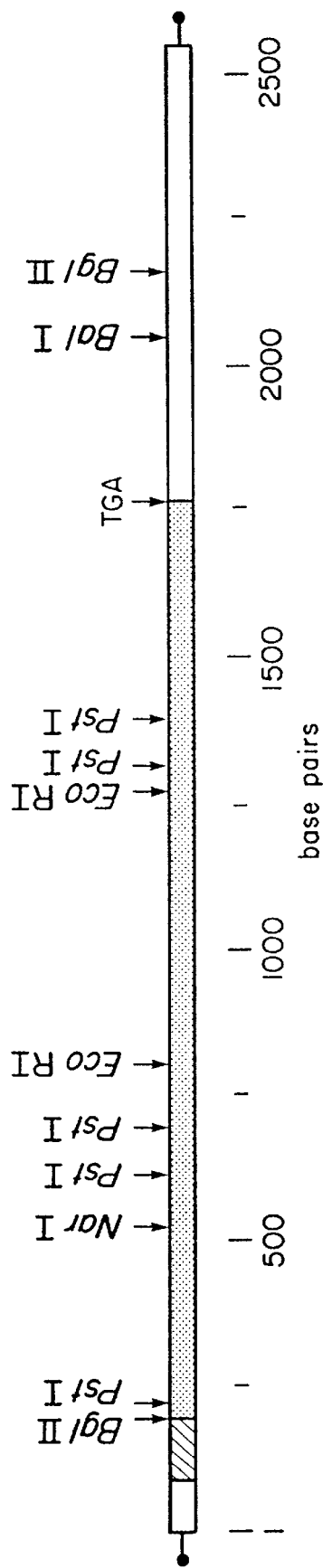
FIG. 4 is a restriction endonuclease map of the full length human t-PA cDNA.

FIG. 4 is a restriction endonuclease map of the full length human tissue plasminogen activator cDNA. The number and size of fragments produced by restriction endonuclease cleavage was estimated by electrophoresis through 6 percent acrylamide gels. Positions of sites were confirmed by nucleic acid sequence (presented in FIG. 5). The coding region of the largest open reading frame is boxed and the hatched region represents the putative signal peptide sequence, while the stipled region represents the putative mature tissue plasminogen activator sequence (527 amino acids). The 5' end of the mRNA is to the left while the 3' end is to the right.

FIGS. 5A, 5B, and 5C illustrate the nucleotide sequence and deduced amino acid sequence of the full length human tissue plasminogen activator cDNA. The 35 amino acids (−35 to −1) preceding the mature sequence is depicted as an uninterupted sequence. It is believed that this 35-amino acid sequence is comprised of a hydrophilic "pro" sequence, preceding serine (+1) of the mature protein, of about 12 to 15 amino acids, in turn preceded by a "conventional" hydrophobic signal (extending 5' to −35). This type of pre-pro structure on secreted proteins has been described previously, e.g. with preproalbumin. Assuming this theory, all of the secreted tissue plasminogen activator molecules will start with the serine (+1) as the amino-terminus. A second theory is that the hydrophilic sequence could be involved with the function of tissue plasminogen activator in a manner analogous to that observed with plasminogen where a peptide of 10,000 daltons can be cleaved from the amino terminal portion of native plasminogen (Glu-plasminogen, named for the amino terminal residue), resulting in a smaller molecule, with a new amino terminus, designated Lys-plasminogen. Lys-plasminogen is more easily activated to plasmin, and also has a greater affinity for fibrin than Glu plasminogen. Plasmin has been shown to catalyze the conversion of Glu- to Lys-plasminogen. This type of control mechanism results in a "positive feedback" mechanism. The first amounts of plasmin formed, beside degrading fibrin, also result in the generation of plasminogen molecules which are more easily activated, and also bind tighter to their substrate, than native plasminogen. The result is a faster degradation of fibrin. The hydrophilic peptide of tissue plasminogen activator could be involved in a similar mechanism, its cleavage resulting in modified binding of the enzyme to fibrin. In any event the 35 amino acid sequence is considered a presequence of the mature protein.

Figure 6:
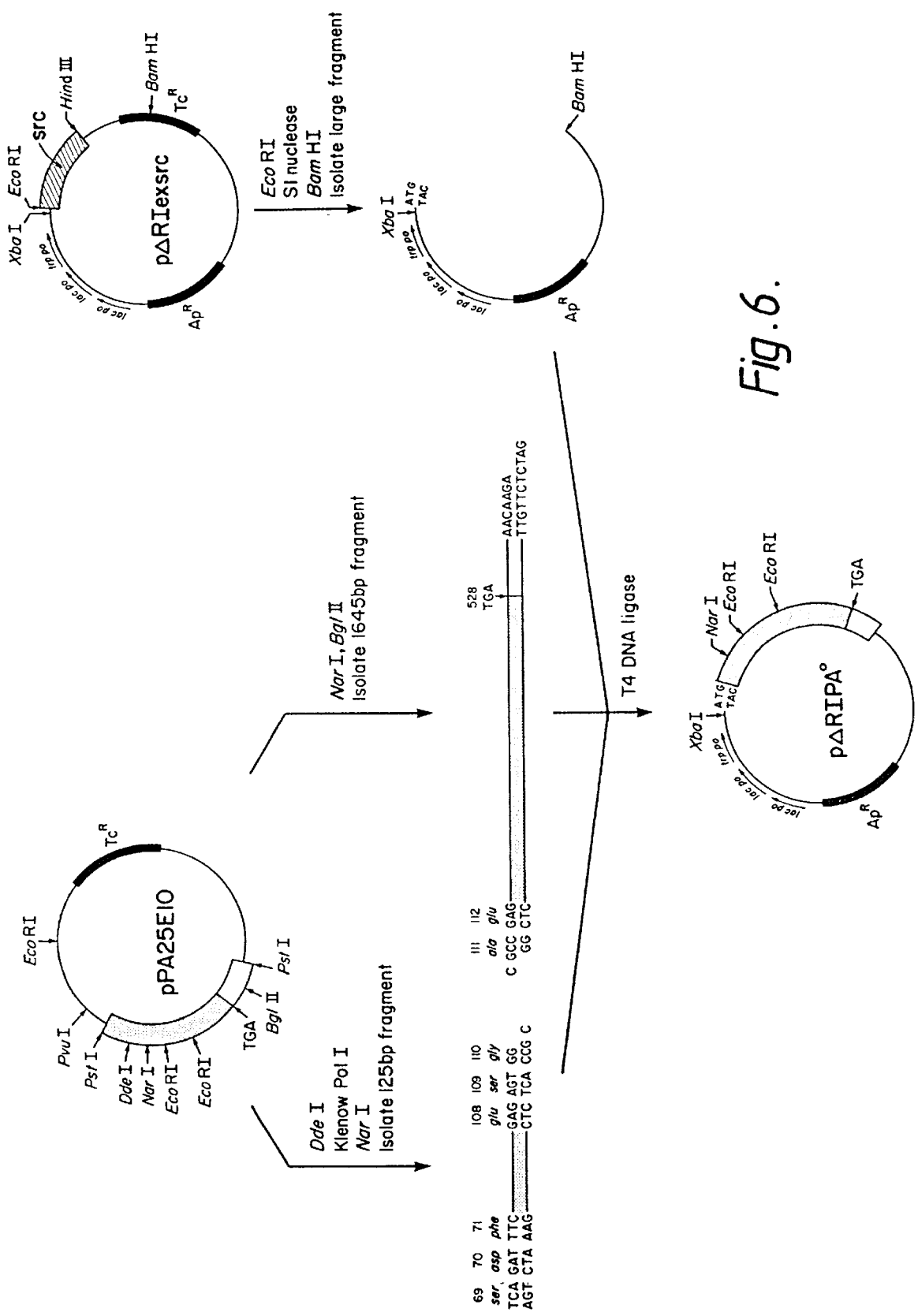
FIG. 6 is a schematic of the construction of the expression plasmid pΔRIPA*.

FIG. 6 is a schematic diagram of the construction of a tissue plasminogen activator expression plasmid pΔRIPA●. The starting plasmid pPA25E10 was first digest with PstI to isolate a 376 bp. fragment that was then digested as shown in the figure.

Figure 7:
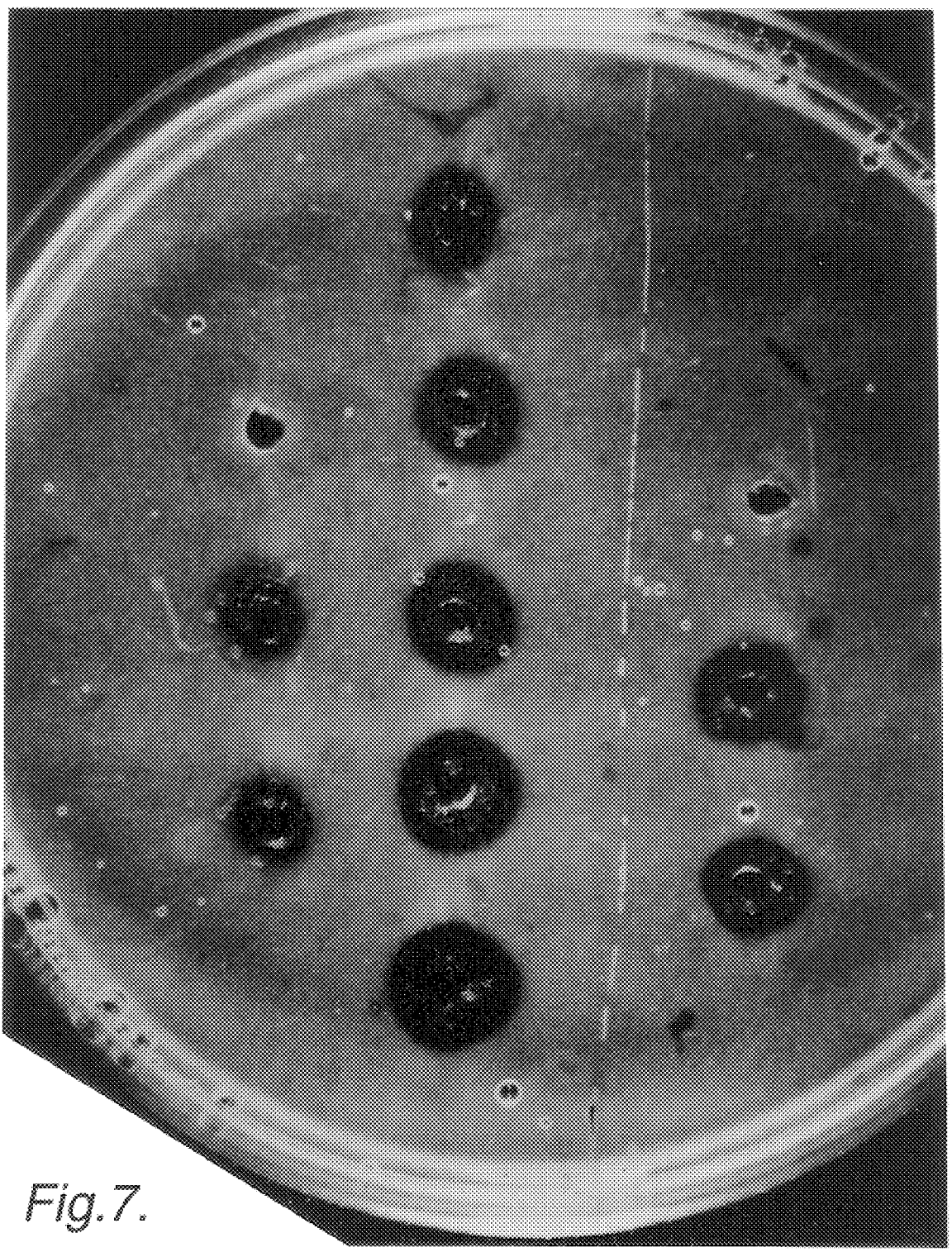
FIG. 7 shows the results of a fibrin plate assay for fibrinolytic activity of E. coli cells transformed with pΔRIPA*.

FIG. 7 shows the result of a fibrin plate assay for fibrinolytic activity of the expression product obtained vial pΔRIPA$^{574}$ in transformed cells.

Figure 8:
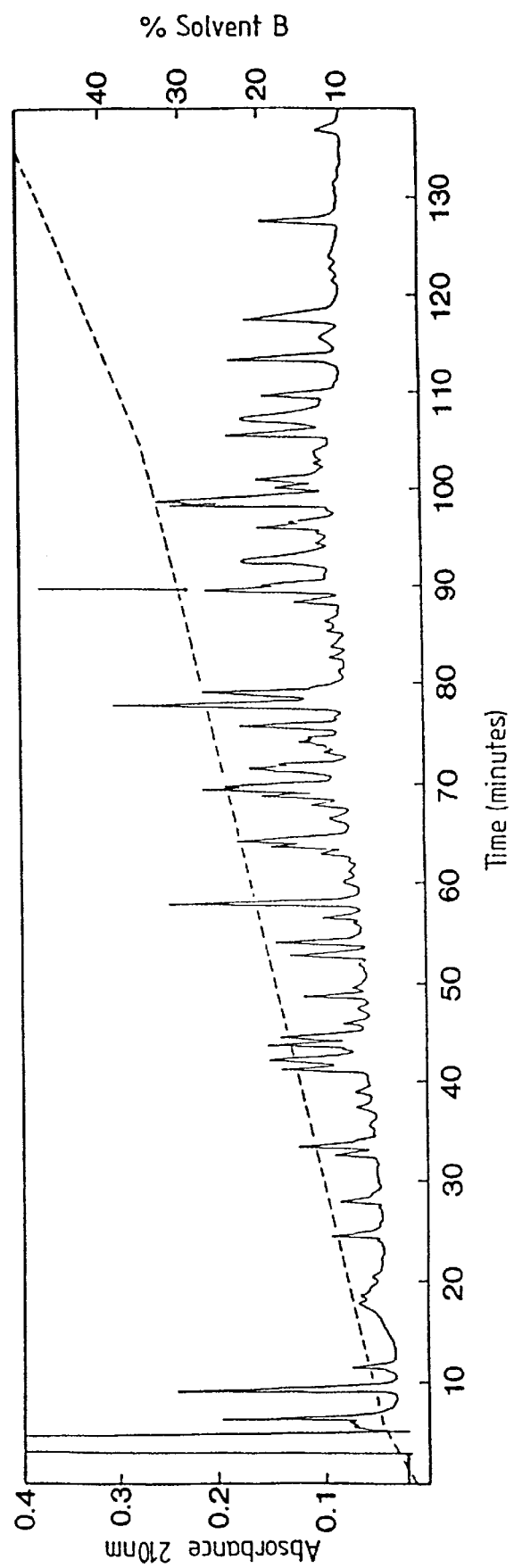
FIG. 8 is an HPLC trace of peptides from human t-PA trypsin digest.

FIG. 8 is an HPLC trace of peptides from tissue plasminogen activator (hereof) trypsin digest (Absorbance at 210 nm). The arrow identifies the peak corresponding to the peptide used to design the nucleotide probed used with the colony library. The peptide represented by this peak was found to have the entire sequence: L-T-W-E-Y-C-D-V-P-S-C-S-T-C-G-L. The other major peaks likewise were sequenced and found to confirm the correct amino sequence of human tissue plasminogen activator. The peptide one letter code referring to amino acid designations is as follows:

| Asp | D | Aspartic acid | Ile | I | Isoleucine |
|-----|---|---------------|-----|---|------------|
| Thr | T | Threonine | Leu | L | Leucine |
| Ser | S | Serine | Tyr | Y | Tyrosine |
| Glu | E | Glutamic acid | Phe | F | Phenylalanine |
| Pro | P | Proline | His | H | Histidine |
| Gly | G | Glycine | Lys | K | Lysine |
| Ala | A | Alanine | Arg | R | Arginine |
| Cys | C | Cysteine | Trp | W | Tryptophan |
| Val | V | Valine | Gln | Q | Glutamine |
| Met | M | Methionine | Asn | N | Asparagine |

Figure 9:
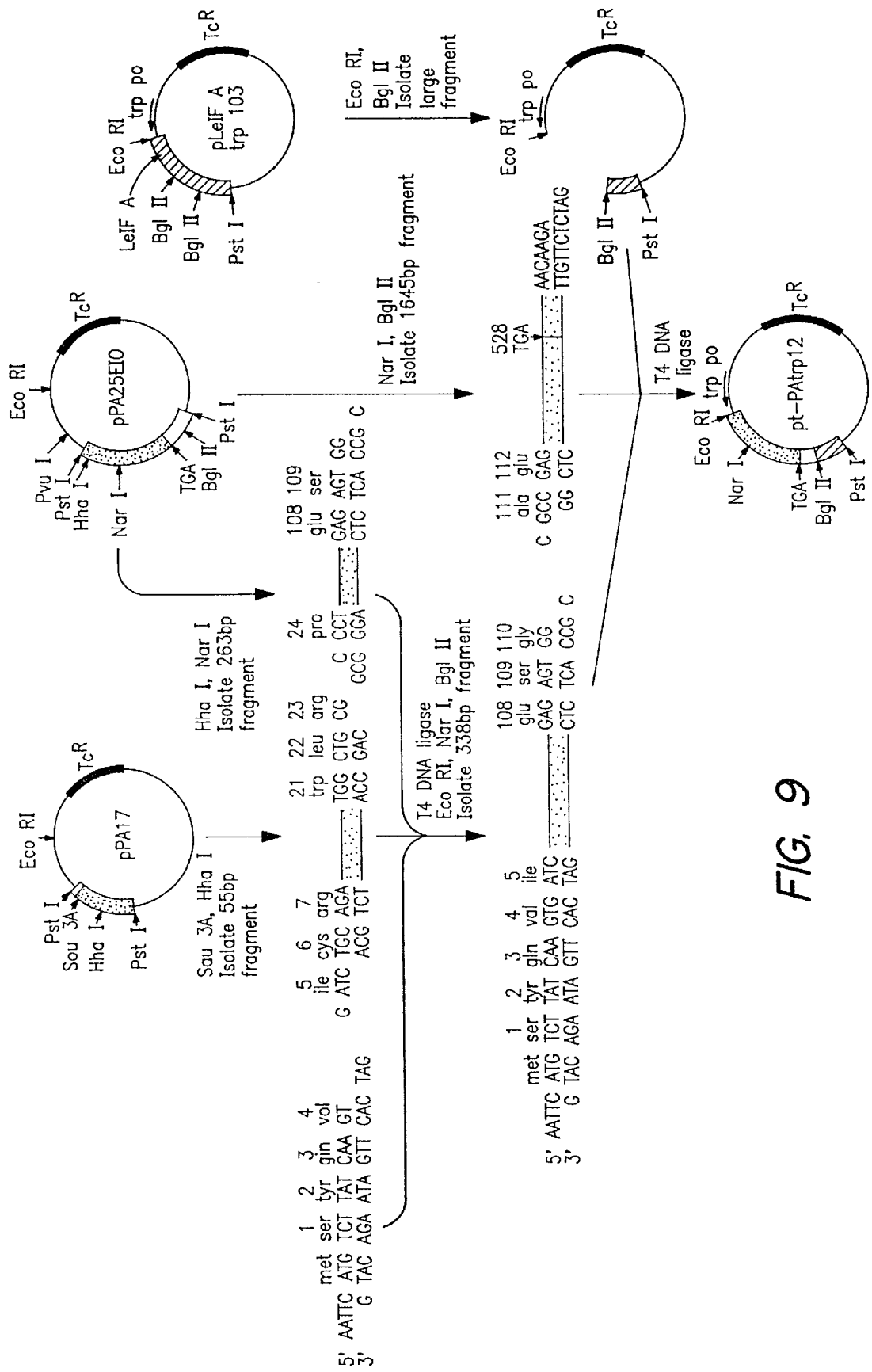
FIG. 9 shows the construction of a plasmid coding for the direct expression of mature human t-PA in E. coli.

FIG. 9 depicts the construction of a plasmid coding for the direct expression of mature human tissue plasminogen activator in $E.$ $coli.$ 50 µg of plasmid pPA17 was digested with Sau3AI, HincII and HhaI and electrophoresed on a 6 percent polyacrylamide gel. Approximately 0.5 µg of the 55 bp Sau3AI-HhaI fragment was recovered. Similarly, approximately 3 µg of the 263 bp HhaI-NarI fragment was purified from 80 µg of clone pPa25E10 by first isolating a 300 bp PstI-NarI fragment and then digesting this fragment with HhaI. All digests were performed at 37° C. for 1 hour and the reaction products resolved and electroeluted from 6 percent polyacrylamide gels. The two indicated deoxyligonucleotides 5' dAATTCATGTCTTATCAAGT (I) and 5' GAT-CACTTGATAAGACATG (II) were synthesized by the solid phase phosphotriester method (51). 100 pmole of oligonucleotide II was phosphorylated in a 30 µl reaction mixture containing 60 mM Tris (pH 8), 10 mM MgCl$_2$, 15 mM β-mercaptoethanol and 50 µCi [γ$^{32}$P]ATP (Amersham 5,000 Ci mmol$^{-1}$) 12 units of T4 polynucleotide kinase were added abd tge reactuib allowed to proceed at 37° C. for 15 min. One µl of 10 mM ATP and 12 units of T4 kinase were then added and the reaction allowed to proceed for an additional 30 min. After phenol/CHCl$_3$ extraction, the phosphorylated oligomer II and the 5' hydroxyl oligomer I were combined with 0.5 µg of the eluted 55 bp Sau3AI-HhaI fragment and 2 µg of the 263 bp HhaI-NarI fragment and ethanol precipitated. These fragments were ligated at room temperature for 4 hours in 60 µl of 20 mM Tris-HCl (pH 7.5), 10 mM MgCl$_2$, 10 mM dithiothreitol, 0.5 mM ATP and 1000 units of T4 DNA ligase. The mixture was digested for 1 hour with 48 units of NarI, 20 units of EcoRI and 40 units of BglII (to eliminate polymerization through ligation of cohesive Sau3AI termini) and electrophoresed on a 6 percent gel. The 338 bp product (approximately 0.1 µg) was recovered by electroelution. The remainder of the t-PA coding sequences (amino acids 111-528) were isolated on a 1645 bp fragment by digesting plasmid pPA25E10 with NarI and BglII. The plasmid pLeIFAtrp103 is a derivative of the plasmid pLe-IFA25 (52) in which the EcoRI site distal to the LeIF A gene has been removed (53). Three µg of pLeIFAtrp103 were digested with 20 units of EcoRI and 20 units of BglII for 90 min. at 37° C., electrophoresed on a 6 percent polyacrylamide gel and the large (~4,200 bp) vector fragment was recovered by electroelution. For the final construction, 80 ng of EcoRI-BglII pLeIFAtrp103 was ligated with 100 ng of the 1645 bp NarI-BglII fragment and 20 ng of the 338 bp EcoRI-NarI fragment for 10 hours at room temperature. This ligation mixture was used to transform $E.$ $coli$ K-12 Strain 294. Plasmid DNA was prepared from 38 of these transformants and digested with EcoRI. Ten of these plasmids contained the desired 600 bp and 472 bp EcoRI fragments. DNA sequence analysis verified that one of these plasmids (pt-PAtrp12) had the desired nucleotide sequence at the junctions between the trp promoter, synthetic DNA and cDNA.

Figure 10:
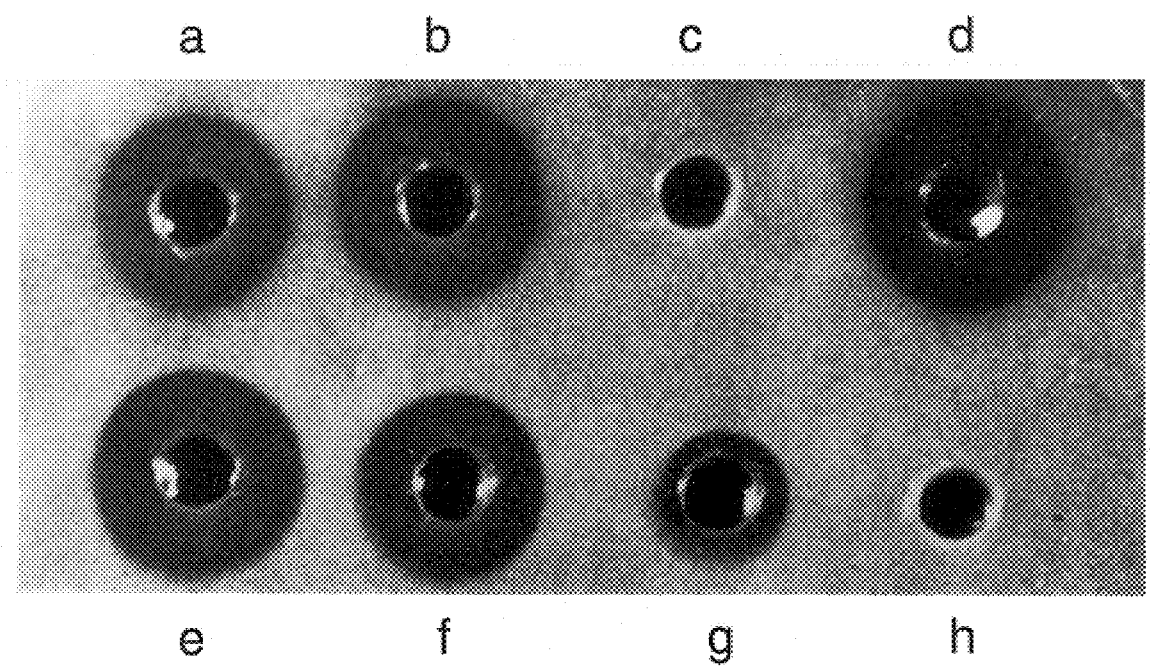
FIG. 10 shows the results of a fibrin plate assay for fibrinolytic activity of the human t-PA produced by FIG. 11 shows the construction of DHFR (mutant or wild type)/t-PA encoding plasmids suitable for transforming into mammilian tissue culture cells.

FIG. 10 shows the result of a fibrin plate assay for fibrinolytic activity of a tissue plasminogen activator expression product hereof. An overnight culture of E. coli W3110 (ATCC 27325) containing a t-PA expression vector in Luria broth containing 5 μg ml$^{-1}$ tetracycline was diluted 1:100 in M9 medium containing 0.2 percent glucose, 0.5 percent casamino acids and 5 μg ml$^{-1}$ tetracycline. The cells were grown at 37° C. to an A$_{550}$ of 0.2 and indole acrylic acid was added to a final concentration of 20 μg/ml. Samples were collected by centrifugation at A$_{550}$=0.5–0.6 (~2×10$^8$ cells ml$^{-1}$) and immediately frozen. The cell pellets were suspended in 6M guanidine hydrochloride at 5×10$^8$ cells/ml, sonicated for 10 sec, incubated at 24° for 30 min and then dialyzed for 4 hrs against 25 mM Tris-HCl pH 8.0, 250 mM NaCl, 0.25 mM EDTA and 0.01 percent Tween 80. After dialysis the samples were centrifuged at 13,000 xg for 2 min and 10 μl of the supernatants analyzed for tissue plasminogen activator activity. Following the procedure of Grannelli-Piperno and Reich (87), the plate was incubated for 3.5 hours at 37° C. and lysis zones measured.

Plasmin produces a clear lysis zone in the fibrin plate and the area of this zone can be correlated to the amount of tissue plasminogen activator in the sample.

E.1.B Source of Tissue Plasminogen Activator mRNA

Human melanoma cells (Bowes melanoma cell line, ATCC accession number CRL 9607) were used. The melanoma cells were cultured to confluent monolayers in 100 ml Earles Minimal Essential Media supplemented with sodium bicarbonate (0.12 percent final concentration), 2 mM glutamine and 10 percent heat-inactivated fetal calf serum. To confirm that the melanoma cells were actively producing human tissue plasminogen activator, human melanoma cells were cultured to confluency in a 24 well microtiter dish. Either in the presence of absence of 0.33 μM the protease inhibitor aprotinin, the cells were washed once with phosphate buffered saline and 0.3 ml of serum free methionine free medium was added. 75 μCi of [$^{35}$S]-methionine was added and the cells were labeled at 37° C. for 3 hours. At the end of the 3 hour labelling period the media was removed from the cells and treated with either tissue plasminogen activator specific IgG or pre-immune serum for immunoprecipitation (54). The immunoprecipitated products were displayed by electrophoreses on a 10 percent SDS-acrylamide gel. The slab gel was fixed, dried and subjected to fluorography.

E.1.C Messenger RNA Isolation and Size Fractionation

Total RNA from melanoma cell cultures was extracted essentially as reported by Ward et al. (55). Cells were pelleted by centrifugation and then resuspended in 10 mM NaCl, 10 mM Tris-HCl pH 7.5, 1.5 mM MgCl$_2$. Cells were lysed by the addition of NP-40 (1 percent final concentration), and nuclei were pelleted by centrifugation. The supernatant contained the total RNA which was further purified by multiple phenol and chloroform extractions. The aqueous phase was made 0.2 M in NaCl and then total RNA was precipitated by the addition of two volumes of ethanol. Oligo-dT cellulose chromotography was utilized to purify mRNA from the total RNA preparations (54). Typical yields from 10 grams of cultured melanoma cells were 5 to 10 milligrams of total RNA and 50–200 micrograms of Poly(A) plus mRNA.

Fractionation of PolyA$^+$ mRNA (200 μg) (56) was performed by electrophoresis through urea-agarose gels. The slab agarose gel (57, 58) was composed of 1.75 percent agarose, 0.025 M sodium citrate, pH 3.8 and 6 M urea. Electrophoresis was performed for 7 hours at 25 milliamps and 4° C. The gel was then fractionated with a razor blade. The individual slices were melted at 70° and extracted twice with phenol and once with chloroform. Fractions were then ethanol precipitated and subsequently assayed by in vitro translation in a rabbit reticulocyte lysate system, Bethesda Research lab. (59,60), supplemented with dog pancreas microsomes as follows: Translations were performed using 25 μCi of [$^{35}$S] methionine and 500 nanograms of each gel slice RNA in a final volume of 30 μl containing 25 mM HEPES, 48.3 mM potassium chloride, 10 mM creatine phosphate. 19 amino acids at 50 mM each, 1.1 mM magnesium chloride 16.6 mM EDTA, 0.16 mM dithiothreitol 8.3 mM hemin, 16.6 μg/ml creatine kinase, 0.33 mM calcium chloride, 0.66 mM EGTA, 23.3 mM sodium chloride.

Incubations were carried out at 30° C. for 90 minutes. Dog pancreas microsomal membranes prepared from rough microsomes using EDTA for removal of the ribosomes (61) were treated with nuclease as described (62) and were present in the translation mixture at a final concentration of 7 A$_{260}$ units/ml. Translation products or immunoprecipitated translation products were analyzed by electrophoresis on 10 percent polyacrylamide gels in sodium dodecyl sulfate as previously described (63). The unstained slab gels were fixed, dried and subjected to fluorography (64).

The resulting translation products from each gel fraction were immunoprecipitated with rabbit anti-human tissue plasminogen activator specific IgG. One major immunoprecipitated polypeptide band was observed in the translation of RNA fraction numbers 7 and 8 (migration of 21 to 245) having a molecular weight of approximately 63,000 daltons. This band was not observed when preimmune IgG was used for immunoprecipitation which suggested these polypeptides were tissue plasminogen activator specific.

E.1.D Preparation of a Colony Library Containing Tissue Plasminogen Activator Sequences Five μg of gel fractionated mRNA (gel slice 7 mRNA) was used for the preparation of double stranded cDNA by standard procedures (52,65,66). The cDNA was size fractionated on a 6 percent polyacrylamide gel. The cDNA greater than 350 base pairs in length (125 ng) was electroeluted. 30 ng of cDNA was extended with deoxy(C) residues using terminal doexynucleotidyl transferase (67) and annealed with 300 ng of the plasmid pBR322 (68) which had been similarly tailed with deoxy(G) residues at the Pst I site (67). The annealed mixture was then transformed into E. coli K12 strain 294 (ATCC No. 31446). Approximately 4,600 transformants were obtained.

E.1.E. Preparation of DNA Probe

Purified human tissue plasminogen activator was obtained according to the procedure of disclosed references (19, 20).

The molecule was scanned in order to locate regions best suited for making synthetic probes, as follows:

To make the proteins susceptible to digestion by trypsin it was reduced and carboxymethylated. A 2 mg sample of tissue plasminogen activator was first dialyzed against 0.01 percent Tween 80 over night at room temperature. The lyophilized protein was then dissolved in 12 ml of 0.56 M Tris-HCl buffer (pH 8.6), 8 molar in urea and 5 mM EDTA. The disulfide bonds were reduced by the addition of 0.1 ml of β-mercaptoethanol. This reaction was carried out under nitrogen for 2 hours at 45° C. The reduced disulfides were alkylated to the carboxymethyl derivative by the addition of 1.0 ml Of 1.4 M iodoacetic acid in 1N NaOH. After 20 min at room temperature the reaction was stopped by dialysis against 0.01 percent Tween 80 for 18 hours at room temperature and lyophilized.

The resulting lyophilized carboxymethylated protein was redissolved in 3 ml of 0.1 M sodium phosphate buffer (pH 7.5). Trypsin (TPCK) was added (1 to 50 ratio) and digested at 37° C. Aliquots (0.1 ml) were taken at 3 hours, 6 hours, and 12 hr. A second addition of trypsin was made at 12 hr. The reaction was stopped after 24 hr by freezing the sample until it could be injected on the HPCL. The progress of the digestion was determined by SDS gels on the aliquots. All gels were blank except for a faint band on the 3 hour aliquot. This indicated that the 24 hour digestion was complete and no large peptides remained.

A sample (ca. 0.5 ml) was injected into a high resolution Altex C-8 ultrasphere 5μ column with two runs. A gradient of acetonitrile was made gradual (1 percent to 5 percent in 5 min, 5 percent to 35 percent in 100 min, 35–50 percent in 30 min). In one of the two preparative runs, the eluant was monitored at two wavelengths (210 nm and 280 nm). The ratio of the two wavelength absorptions was used to indicate the trytophan containing peptides.

The peptide peaks most likely to contain tryptophan, or that were believed useful for other reasons, were sequenced first. This enabled the determination of the sequence around most of the tryptophans. After sequencing about 25 of the best possible peptide peaks, all the sequence data that could be aligned was pooled to obtain a preliminary model of the primary structure of tissue plasminogen activator. From this data and model, several possible probes were located.

E.1.F Identification of Bacterial Clones Containing Tissue Plasminogen Activator cDNA Sequences The colonies were individually inoculated into wells of microtiter plates containing LB (93)+5 μg/ml tetracycline and stored at −20° C. after addition of DMSO to 7 percent. Two copies of the colony library were grown up on nitrocellulose filters and the DNA from each colony fixed to the filter by the Grunstein Hogness procedure (69).

The $^{32}$P-labelled—TC($_G^A$)CA($_G^A$)TA($_T^C$)TCCCA probe was prepared (from the synthetic oligomer) (W-E-Y-C-D) 14-mer pool as described above. Filters containing 4,600 transformants were prehybridized for 2 hours at room temperature in 50 mm sodium phosphate pH 6.8, 5× SSC (80), 150 μg/ml sonicated salmon sperm DNA, 5× Denhardt's solution (85) 10 percent formamide and then hybridized with 50× 10$^6$ counts per minute of the labelled probe in the same solution. After an overnight incubation at room temperature, the filters were washed 3 times at room temperature in 6× SSC, 0.1 percent SDS for 30 minutes, once in 2× SSC and then exposed to Kodak XR-5 x-ray film with Dupont Lightning Plus intensifying screens for 16 hours.

Plasmid DNA was isolated by a rapid method (71) from all colonies showing a positive hybridization reaction. The cDNA inserts from these clones were then sequenced after subcloning fragments into the M13 vector mp 7 (73) and by the Maxam Gilbert chemical procedure (74). FIG. 3 displays filter number 25 showing the hybridization pattern of a positive tissue plasminogen activator clone. The cDNA insert in clone 25E10 was demonstrated to be the DNA coding for tissue plasminogen activator by comparing its amino acid sequence with peptide sequence (See Supra) obtained from purified tissue plasminogen activator and by its expression product produced in E. coli as described in more detail infra. The cDNA insert of clone 25E10 (plasmid pPA25E10) was 2304 base pairs in length with the longest open reading frame encoding a protein of 508 amino acids (MW of 56,756) and containing a 772 bp 3' untranslated region. This cDNA clone lacked the N-terminal coding sequences.

Bacterial clone E. coli (pP25E10), as well as a sample of plasmid pPA252E10, have been deposited with the American Type Culture Collection and accorded accession numbers 67587 and 40401, respectively.

E.1.G Direct Expression of a Human Tissue Plasminogen Activator Clone in E. coli With reference to FIG. 6, 50 μg of pPA25E10 (supra) were digested with Pst I and the 376 bp fragment isolated by electrophoresis on a 6 percent polyacrylamide gel. Approximately 3 μg of this fragment was isolated from the gel by electroeluting, digested with 30 units of Dde I for 1 hr at 37° phenol and chloroform extracted, and ethanol precipitated. The resulting Dde I sticky ends were extended to blunt ends by adding 5 units of DNA polymerase I (Klenow fragment) and 0.1 mM each of dATP, dCTP, dGTP, dTTP to the reaction mixture and incubating at 4° C. for 8 hours. After extraction with phenol and chloroform, the DNA was digested with 15 units of Nar I for 2 hours and the reaction mixture electrophoresed on a 6 percent polyacrylamide gel. Approximately 0.5 μg of the desired 125 pb blunt end Nar I fragment was recovered. This fragment codes for amino acids number 69 through 100 of the mature full length tissue plasminogen activator protein.

For isolation of the 1645 bp Nar I-Bgl II fragment, 30 μg of pPA25E10 were digested with 30 units of Nar I and 35 units of Bgl II for 2 hours at 37° and the reaction mixture electrophoresed on a 6 percent polyacrylamide gel. Approximately 6 μg of the desired 1645 bp Nar I-Bgl II fragment were recovered.

The plasmid pdeltaR1amide gel. Approximately 6 μg of the desired 1645 bp Nar I-Bgl II fragment were recovered.

The plasmid pdeltaRlSRC is a derivative fo the plasmid pSRCex16 (79) in which the Eco R1 sites proximal to the trp promoter and distal to the SRC gene have been removed by repair with DNA polymerase I (28), and the self-complementary oligodeoxynucleotide AATTATGAAT-TCAT (synthesized by the phosphotriester method (75) was inserted into the remaining Eco RI sile immediately adjacent to the Xba I site. 20 μg of the pdeltaR1SRC were digested to completion with Eco RI, phenol and chloroform extracted, and ethanol precipitated. The plasmid was then digested with 100 units of nuclease S1 at 16° C. for 30 minutes in 25 mM sodium acetate (pH 4.6). 1 mM ZnCl$_2$ and 0.3 M NaCl to create a blunt end with the sequence ATG. After phenol and chloroform extraction and ethanol precipitation, the DNA was digested with Bam H1, electrophoresed on a 6 percent polyacrylamide gel, and the large (4,300 bp) vector fragment recovered by electroelution.

The expression plasmid was assembled by ligating together 0.2 μg of vector, 0.06 μg of the 125 bp blunt end—Nar I fragment and 0.6 μg of the 1645 bp Nar I-Bgl II fragment with 10 units of T$_4$ DNA ligase for 7 hours at room temperature and used to transform E. coli strain 294 (ATCC No. 31446) to amplicillin resistance. Plasmid DNA was prepared from 26 of the colonies and digested with Xba I and Eco RI. Twelve of these plasmids contained the desired 415 bp Xba I-Eco RI and 472 bp Eco RI-fragments. DNA sequence analysis verified that several of these plasmids had an ATG initiation codon correctly placed at the start of amino acid number 69 (serine). One of these plasmids, PΔRIPA® was tested and produced the desired tissue plasminogen activator (FIG. 7).

Bacterial clone E. coli (pΔRIPA$^o$), as well as a sample of plasmid pΔRIPA$^o$, have been deposited with the American Type Culture Collection and accorded accession number 67585 and 40400, respectively.

E.1.H Full Length Tissue Plasminogen Activator cDNA
a.) Preparation of a Colony Library Containing N-terminal Tissue Plasminogen Activator Sequences 0.4 μg of the synthetic oligonucleotide 5' TTCTGAGCA-CAGGGCG 3' was used for priming 7.5 μg of gel fraction number 8 mRNA (supra) to prepare double stranded cDNA by standard procedures (65, 66). The cDNA was size fractionated on a 6 percent polyacrylamide gel. A size fraction greater than 300 base pairs (36 ng) was electroeluted. 5 ng cDNA was extended with deoxy(C) residues using terminal deoxycytidyl transferase (67) and annealed with 50 ng of the plasmid pBR322 (68) which had been similarly tailed with deoxy(G) residues at the Pst I site (67). The annealed mixture was then transformed into E. coli K12 strain 294. Approximately 1,500 transformants were obtained.

b.) Southern Hybridization of Human Genomic DNA

Since the cDNA priming reaction had been done using a synthetic fragment that hybridized 13 base pairs from the N-terminal of clone pPA25E10, no convenient restriction fragment was available in this 29 base pair region (which includes the 16-mer sequence) for screening the cDNA clones. Therefore, it was necessary to isolate a human tissue plasminogen activator genomic clone in order to identify any primer extended cDNA clones containing N-terminal tissue plasminogen activator coding sequences.

The first step in this process involved establishing the fact that only a single homologous tissue plasminogen activator gene is present in human genomic DNA. To determine this, a Southern hybridization was performed. In this procedure (77), 5 $\mu$g of high molecular weight human lymphoctye DNA (prepared as in 80) was digested to completion with various restriction endonucleases, electrophoresed on 1.0 percent agarose gels(81) and blotted to a nitrocellulose filter (77). A $^{32}$P-labelled DNA probe was prepared (76) from the 5' end of the cDNA insert of the pPA25E10 (a 230 bp Hpa II-Rsa I fragment) and hybridized (82) with the nitrocellulose filter. $35 \times 10^6$ counts per minute of the probe were hybridized for 40 hours and then washed as described (82). Two endonuclease digestion patterns provide only a single hybridizing DNA fragment: Bgl II (5.7 Kbp) and Pvu II (4.2 Kbp). Two hybridizing DNA fragments were observed with Hinc II (5.1 Kbp and 4.3 Kbp). Taken together, these data suggest the presence of only a single tissue plasminogen activator gene in the human genome, and that this gene contains at least one intervening sequence.

c). Screening of the Human $\lambda$ Phage Library for Tissue Plasminogen Activator Genes.

The strategy used to identify $\lambda$ phage recombinants carrying tissue plasminogen activator genes consisting in detecting nucleotide homology with a radioactive probe prepared from the tissue plasminogen activator plasmid pPA25E10. One million recombinant $\lambda$ phage were plated out on DP 50 Sup F at a density of 10,000 pfu/15 cm plate, and nitrocellulose filter replicas were prepared for each plate by the method of Benton and Davis (78). A $^{32}$P-labelled DNA probe was prepared by standard procedures (83) from a 230 base pair Hpa II-Rsa I fragment located 34 base pairs from the 5' end of the clone p25E10. Each nitrocellulose filter was prehybridized at 42° for 2 hours in 50 mM sodium phosphate (pH 6.5), 5× SSC (77), 0.05 mg/ml sonicated salmon sperm DNA, 5× Denhardt's solution (84), 50 percent formamide and then hybridized with $50 \times 10^6$ counts per minute of the labelled probe in the same solution containing 10 percent sodium dextran sulfate (85). After an overnight incubation at 42° C., then filters were washed 4 times at 50° in 0.2× SSC, 0.1 percent SDS for 30 minutes, once in a 2×SSC at room temperature and then exposed to Kodak XR-5 X-ray film with Dupont Cronex intensifying screens overnight. A total of 19 clones were obtained which hybridized with the probe. Phage DNA was prepared as previously described (86) from 6 recombinants. $\lambda$ Clone C was selected for preparation of a Pvu II fragment for colony screening. 30 $\mu$g of DNA was digested with Pvu II for 1 hour at 37°, and electrophoresed on 1.0 percent agarose gels. A 4.2 Kilobase pair fragment previously shown to contain tissue plasminogen activator sequences was electroeluted and purified. A $^{32}$P labelled probe was prepared by standard procedures (83) for colony hybridizations as described infra.

d.) Screening of Colony Library for 5' Tissue Plasminogen Activator Sequences.

The colonies were transferred from plates and grown on nitrocellulose filters and the DNA from each colony fixed to the filter by the Grunstein—Hogness procedure (69). A $^{32}$P-labelled probe was made by calf-thymus priming (83) a 4.2 kilobase pair Pvu II fragment from an isolated tissue plasminogen activator $\lambda$ genomic clone. Filters containing the 1,500 transformants were hybridized with $112 \times 10^6$ cpm of $^{32}$P-genomic Pvu II fragment. Hybridization was for 16 hours using conditions described by Fritsch et. al (82). Filters were extensively washed and then exposed to Kodak XR-5 X-ray film with Dupont Lightning-Plus intensifying screens for 16–48 hours. Eighteen colonies clearly hybridized with the genomic probe. Plasmid DNA was isolated from each of these colonies and was bound to nitrocellulose filters and hybridized with the $^{32}$P-labelled synthetic oligonucleotide (16-mer) used of the original priming reaction. Of the 18 clones, seven hybridized with the kinased 16-mer. Upon sequence analysis after subcloning fragments into the m13 vector mp$^7$ (73), one clone (pPA17) was shown to contain the correct 5' N terminal region of tissue plasminogen activator, a signal leader sequence and an 84 pb 5' untranslated region. From the two clones pPA25E10 and pPA17 the complete nucleotide sequence FIG. 5 and restriction pattern (FIG. 4) of a full length tissue plasminogen activator clone were determined.

Bacterial clone E. coli (pPA17), as well as a sample of plasmid pPA17, have been deposited with the American Type Culture Collection and accorded accession numbers 67586 and 40402, respectively.

The native tissue plasminogen activator molecule has the potential to be stabilized by 17 disulfide bridges based on homology with other serine proteases. There are four potential N-glycosylation sites, three located in the "kringle" regions at $asn_{117}$, $asn_{184}$, $asn_{218}$ and one potential site in the light chain region, at $asn_{448}$. Variations in the structure of the oligosaccharide ligands may be responsible for the different molecular forms (65,000 and 63,000 mol. wt. species).

E.1.I Direct Expression of Full Length Tissue Plasminogen Activator cDNA Clone in E. coli A reconstruction of the entire coding sequence was possible employing the common HhaI restriction endonuclease site shared by both partial clones pPA17 and pPA25E10. A 55 bp Sau3AI-HhaI restriction fragment corresponding to amino acids 5–23 was isolated form the plasmid pPA17. The Sau3AI restriction site was located at codon four of the presumed mature coding sequence and was used to remove the signal peptide coding region. A 263 bp HhaI-NarI fragment (coding for amino acids 24–110) was also isolated from plasmid pPA25E10. Two synthetic deoxyoligonucleotides were designed which restore the codons for amino acids 1–4, incorporate an ATG translational initiation codon and create an EcoRI cohesive terminus. These three fragments were then ligated together to form a 338 bp fragment coding for amino acids 1–100. this fragment and a 1645 bp NarI-BglII fragment from pPA25E10 were then ligated between the EcoRI and BglII sites of the plasmid pLeIFAtrp103 (53) to give the expression plasmid pt-PAtrp12. The cloned t-PA gene is transcribed under the control of a 300 bp fragment of the E. coli trp operon which contains the trp promoter, operator, and the Shine-Dalgarno sequence of the trp leader peptide but lacks the leader peptide ATG initiation codon (52).

A sample of plasmid pt-PAtrp12 has been deposited with the American Type Culture Collection and accorded accession number 40404.

E.1.J Sequence Analysis

Sequence analysis was based on the Edman degradation. (83b) The sample was introduced into the cup of the Beckman 890B or 890C spinning cup sequencer. Polybrene™ (poly N,N,N$^1$N$^1$-tetramethyl-N-trimethylenehexamethylene diammonium diacetate) was used as a carrier in the cup. (63C) The sequencer was modified with a cold trap and some program changes to reduce background peaks. The reagents were Beckman's sequence grade 0.1 molar Quadrol buffer, phenylisothiocyanate, and heptafluorabutyric acid.

The collected Edman cycles were manually converted to 2-anilino-5-thiazolinone derivatives. The 1-chlorobutane was dried under nitrogen. Then 1.0 N HCl in water was added to the 2-anilino-5-thiazolinone and heated to 70° C. for 10 min to convert it into the 3-phenyl-2-thiohydantoin (PTH derivative). The PTH-amino-acid residue was then dissolved in 50 percent acetonitrile and water and injected into a reverse-phase high-pressure liquid chromatograph. Each PTH-amino acid was then identified by comparison to the retention times of a standard mixture of PTH-amino acids that was introduced into the conversion vial and treated the same way as a cycle from the sequencer.

E.1.K. Assays for Detection of Expression of Tissue Plasminogen Activator

1. Direct Assay of Plasmin Formation

A. Theory

A sensitive assay for tissue plasminogen activator can be obtained by monitoring the tissue plasminogen activator catalyzed conversion of plasminogen to plasmin. Plasmin is an enzyme for which there are chromogenic substrate assays. These assays are based on the proteolytic cleavage of a tripeptide from a chromophoric group. The rate of cleavage is directly related to both the specificity and the concentration of the protease being tested. The basis of the assay is the determination of the amount of plasmin formed following incubation of the tissue plasminogen activator containing solution with a solution of plasminogen. The greater the amount of activator, the greater the amount of plasmin formed. Plasmin is measured by monitoring its cleavage of the chromogenic substrate S2251 (purchased from Kabi Group, Inc., Greenwich, Conn.).

b. Procedure

An aliquot of the sample is mixed with 0.10 ml of 0.7 mgs/ml plasminogen (in 0.05M Tris·HCl, pH 7.4, containing, 0.012 M NaCl) and the volume adjusted to 0.15 ml. The mixture is incubated at 37° C. for 10 minutes, 0.35 ml of S2251 (1.0 mM solution in above buffer) is added, and the reaction continued for 30 minutes at 37° C. Glacial acetic acid (25 µL) is added to terminate the reaction. The samples are centrifuged and the absorbance at 405 nm is measured. Quantitation of the amount of activity is obtained by comparison with a standard unokinase solution. Activity was recorded in Plough units, wherein 90,000 Plough units is equal to the activity exhibited by 1 mg of purified tissue plaminogen activator.

2. Indirect Assay of Plasmin Formation a. Theory

A sensitive assay for tissue plasminogen activator activity has been developed (87). The assay is based on determination of plasmin formation by measuring the extent of plasmin digestion of fibrin in an agar plate containing fibrin and plasminogen. Plasmin produces a clear lysis zone in the fibrin plate. The area of this lysis zone can be correlated to the amount of tissue plasminogen activator in the sample.

b. Procedure

Following the procedure of Granelli-Piperno and Reich (87), the plates were incubated 3.5 hours at 37° C. and lysis zones measured. Quantitation was obtained by comparison to a standard urokinase solution.

E.1.L. Detection of Tissue Plasminogen Activator Activity

1. Bacterial Growth and Sample Preparation.

A colony of E. coli containing the plasmid (pΔRIPA*) was inoculated into a test tube containing 5 mL of LB growth media containing 20 µg/ml amplicillin. The cells were grown overnight at 37° C. An aliquot of this culture was diluted 1:100 into 300 ml of M9 media containing 20 µg/ml amplicillin. The cells were grown in a shaker flask at 37° C. for four hours, with a resulting absorbance at 550 nm of 0.419. The tryptophan analog indole acrylic acid was added to a concentration of 30 µg/ml. The cells were incubated 90 minutes, with a resulting absorbance at 550 nm of 0.628. The cells were harvested by centrifugation and resuspended in 0.8 ml of 0.01 M Tris, pH 8.0, containing 0.01 M EDTA. The resulting suspension was stirred rapidly at room temperature for 18 hours. The sample was centrifuged and the supernatant assayed for tissue plasminogen activator activity.

2. Activity Detection.

Table 1 show the results of the activation of plasminogen by E. coli extracts when assayed. An activity is generated which is dependent on the presence of plasminogen. This activity is not affected by pre-immune serum of a rabbit but is markedly inhibited by antiserum which was raised against purified melanoma cell derived tissue plasminogen activator (88). This demonstrates that the E. coli extracts are producing a plasminogen activating activity which is inhibited by antibodies against the tissue plasminogen activator.

FIG. 7 shows the result of a fibrin plate assay for fibrinolytic activity. A standard amount of urokinase was added to the center row in concentrations, from left to right, of 0.24, 0.14, 0.10, 0.05 and 0.02 Plough Units. The bottom row is samples of natural tissue plasminogen activator, with the same amount of enzyme in each well. The wells contain, from left to right, tissue plasminogen activator, anti-plasminogen activator plus pre-immune serum, and tissue plasminogen activator plus tissue plasminogen activator antibodies. The wells in the top row each contain 8 µl of the recombinant tissue plasminogen activator E. coli extracts. The first well is the extract alone, the second well has preimmune serum added, and the third well has the tissue plasminogen activator antibodies added. It is obvious that the preimmune serum does not affect natural or recombinant tissue plasminogen activator, and that tissue plasminogen activator antibodies inhibit the activity of natural as well as the E. coli extracts. Based on the urokinase standards, the extracts contain slightly less than 2.5 Plough units per ml. This compares favorably with the value obtained in Table 1 of 1.3 Plough units per ml.

Tables 1 and 2 set forth the results of assays performed as described above in E.1.K.1. b.:

TABLE 1

Plasminogen Activation by *E. coli* Extracts of Cultures Containing pAR1PA

| Sample | $A^{405}$ | Percent Activity[1] | Calculated Plough Units/mL |
|---|---|---|---|
| Extract (with no plasminogen) | 0.043 | (0) | |
| Extract | 0.451 | (100) | 1.3 |
| Extract plus preimmune serum | 0.477 | 106 | — |
| Extract plus anti t-PA antibodies | 0.079 | 9 | — |

[1]Percent activity calculated by subtracting the blank (0.043) from the values obtained and dividing by the value obtained from the extract.

FIG. 10 represents the results of a fibrin plate assay performed with extracts from 10 L fermentation cultures of *E. coli* containing a tissue plasminogen activator expressing plasmid. The fibrinolytic activity of the tissue plasminogen activator containing extract is represented in FIG. 10 by Well A. This fibrinolytic activity is inhibited by anti t-PA IgG (Well C) but not by preimmune IgG (Well B) or anti urokinase IgG (Well D) and no activity is seen from an extract prepared from cells containing as a control the leukocyte interferon plasmid pLeIFAtrp103 (Well H).

E.2 Production of tPA Using DHFR Protein with a Low Binding Affinity for MTX

E.2.A Vector Construction

Figure 11:
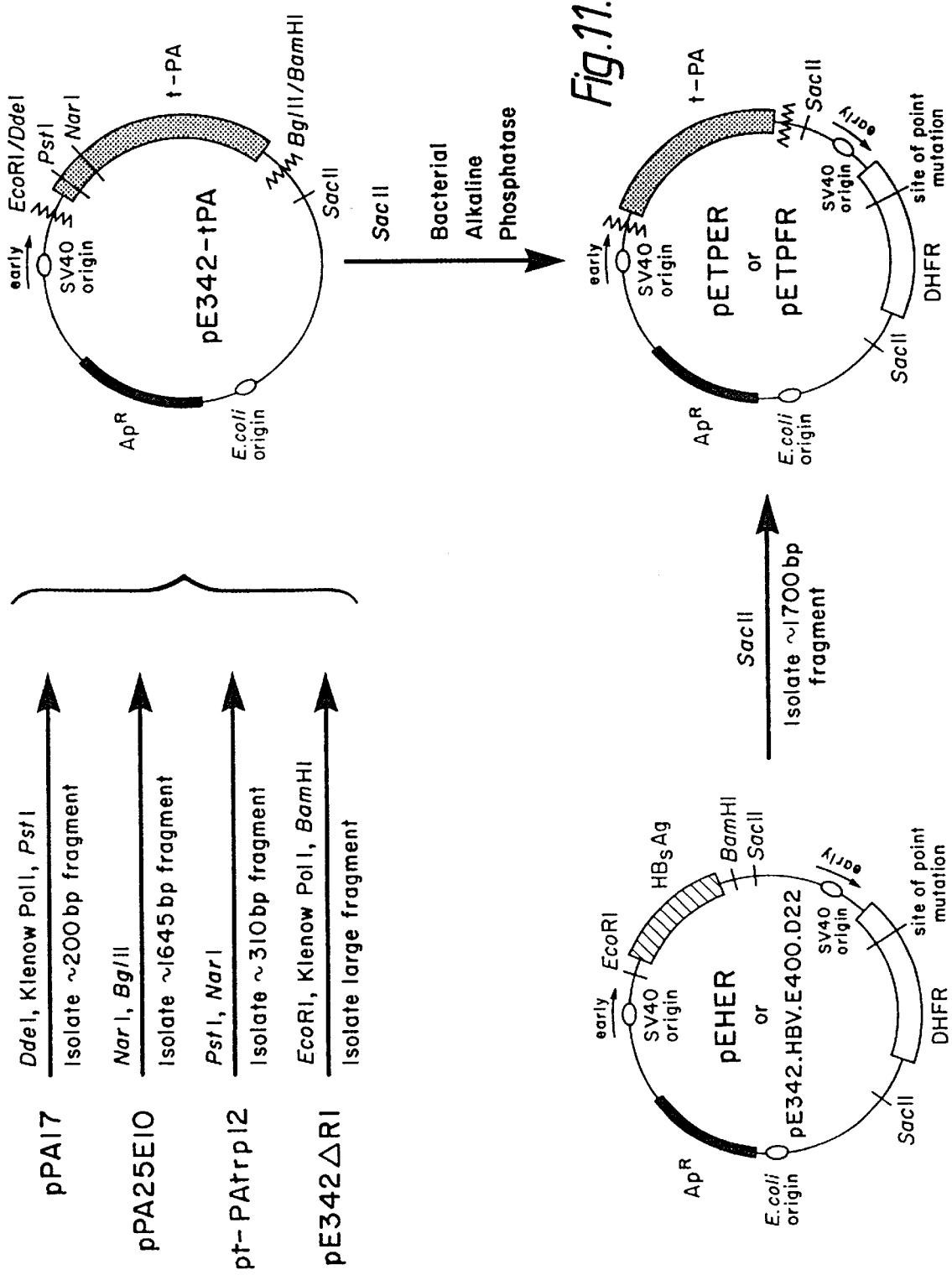

The sequence encoding human tissue plasminogen activator (t-PA) is inserted into an expression plasmid containing a mutant DHFR with low binding affinity for MTX, described in copending application U.S. Ser. No. 459,151, filed Jan. 19, 1983 and now abandoned, corresponding to European Patent Application Publ. No. 117,060, incorporated herein by reference, by the following procedure (see FIG. 11):

Three fragments from overlapping t-PA plasmids, pPA25E10, and pPA17, and pt-PAtrp12 (supra) were prepared as follows: Plasmid pPA17 was digested with Dde I, filled in using Klenow DNA polymerase 1, and subcut with Pst I; the approximately 200 bp fragment containing 5' terminal t-PA sequence thus generated was isolated. The second t-PA fragment was obtained by digesting pt-PAtrp12 with Pst I and NarI and isolating the approximately 310 bp fragment. The third t-PA fragment was obtained by digesting pPA25E10 with Nar I and Bgl II and isolating the approximately 1645 bp fragment which contains, in addition to much of the t-PA coding region, some 3' non-translated sequences.

Plasmid pE342 which expresses HBV surface antigen (also referred to as pHBs348-E) has been described by Levinson et al, patent application Ser. No. 326,980, filed Dec. 3, 1981, now abandoned in favor of continuing application application Ser. No. 603,529 filed Apr. 24, 1984, now U.S. Pat. No. 4,741,901, and corresponding to European Patent Application Publ. No. 73,656, and which is incorporated herein by reference. (Briefly, the origin of the Simian virus SV40 was isolated by digesting SV40 DNA with HindIII, and converting the HindIII ends to EcoRI ends by the addition of a converter (AGCTGAATTC). This DNA was cut with PvuII, and RI linkers added. Following digestion with EcoRI, the 348 base-pair fragment spanning the origin was isolated by polyacrylamide gel electrophoresis and electroelution, and cloned in pBR322. Expression plasmid pHBs348-E was constructed by cloning the 1986 base-pair fragment resulting from EcoRI and BglII digestion of HBV (*Animal Virus Genetics*, (Ch. 5) Acad. Press, N.Y. (1980)) (which spans the gene encoding HBsAg) into the plasmid pML (Lusky et al., *Nature,* 293: 79 (1981) at the EcoRI and BamHI sites. (pML is a derivative of pBR322 which has a deletion eliminating sequences which are inhibitory to plasmid replication in monkey cells). The resulting plasmid (pRI-Bgl) was then linearized with EcoRI, and the 348 base-pair fragment representing the SV40 origin region was introduced into the EcoRI site of pRI-Bgl. The origin fragment can insert in either orientation. Since this fragment encodes both the early and late SV40 promoters in addition to the origin of replication, HBV genes could be expressed under the control of either promoter depending on this orientation (pHBS348-E representing HBs expressed under control of the early promoter). pE342 is modified by partially digesting with Eco RI, filling in the cleaved site using Klenow DNA ploymerase I, and ligating the plasmid back together, thus removing the Eco RI site preceding the SV40 origin in pE342. The resulting plasmid, designated pE342ΔRl, is digested with Eco RI, filled in using Klenow DNA polymerase I, and subcut with Bam HI. After electrophoresing on acrylamide gel, the approximately 3500 bp fragment is electroeluted, phenol-chloroform extracted, and ethanol precipitated as above.

The thus prepared p342E 3500 bp vector, and above described t-PA fragment comprising approximately 2160 bp were ligated together using standard techniques. A plasmid containing the three tPA encoding fragments in the proper orientation was isolated, characterized, and designated pE342-t-PA. This plasmid was digested with Sac II and treated with bacterial alkaline phosphatase (BRL). To provide the DHFR sequence (along with control sequences for its expression) an approximately 1700 bp fragment was generated by SacII digestion of pEHER. (pEHER is a plasmid expressing mutant DHFR described in U.S. Ser. No. 459,151 (supra). This fragment was ligated into the pE342-t-PA plasmid to create PETPAER400, a plasmid which is analagous to pEHER except that the HBsAg coding region has been replaced by the cDNA sequences from t-PA.

E.2.B Expression and Amplification of the t-PA Sequence pETPAER400 (pETPER) was transfected into both dhfr⁻ CHO-DUX B11 cells and DHFR⁺ CHO-K1) (ATCC CCL61) cells by the method of Graham and Van der Eb (supra). transformed dhfr⁻ cells were selected by growth in glycine, hypoxanthine and thymidine deficient medium. Transformed DHFR⁺ cells were selected by growth in ≧100 nM MTX. Colonies which arose on the appropriate selection medium were isolated using cloning rings and propagated in the same medium to several generations.

For amplification cells from the colonies are split into media containing $5 \times 10^4$, $10^5$, $2.5 \times 10^5$, $5 \times 10^5$, and $10^6$ nM MTX and passaged several times. Cells are plated at very low ($10^2$–$10^3$ cells/plate) cell densities in 10 cm dishes and the resulting colonies are isolated.

E.2.C Assay Methods

Expression of t-PA in the transfected amplified colonies may conveniently be assayed by the methods similar to those set forth in E.1.K.1. b (supra).

Coamplification of DHFR and t-PA sequences is assayed by isolating DNA from confluent monolayers of amplified colonies as follows: Confluent monolayers in 150 mm plates are washed with 50 ml sterile PBS and lysed by the addition of 5 ml of 0.1 percent SDS, 0.4 M CaCl$_2$, 0.1 M EDTA, pH 8. After 5–10 minutes, the mixture is removed, phenol extracted, chloroform extracted, and ethanol precipitated. The DNA is resuspended in 1 ml (per 150 mm plate) 10 mM Tris-HCl pH 8, 1 mM EDTA (TE), RNase added to 0.1 mg/ml, and the solution incubated 30 minutes at 37°. SDS is then added to 0.1 percent and pronase (Sigma) is added to 0.5 mg/ml. After 3–16 hours incubation at 37°, the solution is again phenol extracted, chloroform extracted, and ethanol precipitated. The DNA pellet is resuspended in 0.5 ml water and digested with restriction enzymes. Approximately 5–10 μg of digested DNA is electrophoresed in an agarose gel [1 percent agarose in Tris-acetate buffer (40 mM Tris, 1 mM EDTA, made to pH 8.2 with acetic acid)]; Crouse, et al. *J. Biol. Chem.*, 257: 7887 (1982)). After bromphenol blue dye had migrated ⅔ of the way down the gel, the gel is removed and stained with ethidium bromide. After visualzing the DNA with ultraviolet light, the DNA is transferred from the gel to nitrocellulose filters according to the procedure of Southern (*J. Mol. Biol.* 98: 503. (1975)). The filters are then hybridized with a nick translated probe made from the 1700 bp SacII fragment of pEHER (prepared and hybridized as described above), or from the approximately 1970 bp Bgl II fragment of pETPER.

E.3 Production of t-PA in Conjunction with Wild Type DHFR Protein

E.3.A Vector Construction

In a manner analogous to that used in the construction of pETPER, plasmid pETPER was constructed containing the DNA sequence encoding wild type DHFR. The construction was as described in Example E.2.A. except that in place of plasmid pEHER as a source for the DHFR protein gene sequence, the plasmid pE342.HBV.E400.D22 described in copending Genentech Docket No. 100/92 U.S. Ser. No. 459,152, filed Jan. 19, 1983, now U.S. Pat. No. 4,713,339, corresponding to European Patent Application Publ. No. 117,058, incorporated herein by reference, was substituted. The plasmid pE342.HBV.E400.D22 is the same as pEHER except for a single base pair difference between wild type and mutant DHFR. Thus the resulting plasmid pETPFR is analogous in every way to pETPER except that the DNA sequence encoding for wild type DHFR is substituted for that of the mutant.

A sample of plasmid pETPFR has been deposited with the American Type Culture Collection and accorded accession number 40403.

E.3.B Expression of t-PA sequence pETPFR was used to transfect DHFR deficient CHO cells (Urlaub and Chasin (supra)) using the calcium phosphate precipitation method of Graham and Van der Eb. Twenty-one colonies which arose on the selective medium (-HGT) were assayed by detection of plasmin formation as assessed by the digestion of fibrin in an agar plate containing fibrin and plasminogen, described by Granelli-Piperno, et al, *J. Exp. Med.*, 148: 223 (1978).

Four of the most strongly positive clones were then assayed quantitatively for plasmin formation on a per cell basis according to the method set forth in E.1.K.1.b:

Upon such quantitative determination it was found that the four clones tested exhibited the same or comparable t-PA secretion into the medium, determined as units/cell/day. Subclones were prepared by transferring inocula from two of the clones into separate plates containing -HGT medium. Two of the resulting subclones, 18B and 1 were used for further analysis.

E.3.C Amplification and t-PA Production Levels

The above subclones were plated at 2×10⁵ cells per 100 mm plates in 50 nM MTX to promote amplification. Those cells which survived, when assayed as described above, gave, in all cases, about 10 times the unamplified amount of tissue plasminogen activator activity. Two of these clones were chosen for further study and were named 1–15 and 18B–9.

Subclone 1–15 was further amplified by seeding 2×10⁵ cells in 100 mm plates containing 500 nM MTX. Assay of the cells thus amplified yielded a further increase (of about 3 fold) in t-PA production; when assayed quantitatively by the method of C.1.C, levels were in the range of 7×10⁻⁴ units/cell/day. A portion of these amplified cells was then transferred and maintained in the presence of 10,000 nM MTX. Subclones of 1–15, and 18B–9 were further tested after being maintained for approximately 1–2 months at the conditions specified in Table 3.

TABLE 3

| Cell Line | Growth Conditions | ng t-PA/cell/day* |
| --- | --- | --- |
| 1–15$_{500}$ | 500 nM MTX | 28.5 × 10⁻³ |
| 1–15$_{500}$ | 500 nM MTX | 26.0 × 10⁻³ |
| 1–15$_{500}$ | (–HGT medium, no MTX) | 8.3 × 10⁻³ |
| 1–15$_{500}$ | (–HGT medium, no MTX) | 18.0 × 10⁻³ |
| 1–15$_{10,000}$ | 10 μM MTX | 29.3 × 10⁻³ |
| 1–15$_{10,000}$ | 10 μM MTX | 49.0 × 10⁻³ |
| 18B-9 | 50 nM MTX | 14.3 × 10⁻³ |
| 18B-9 | 50 nM MTX | 14.4 × 10⁻³ |
| 18B-9 | (–HGT medium, no MTX) | 14.3 × 10⁻³ |
| 18B-9 | (–HGT medium, no MTX) | 14.4 × 10⁻³ |
| 1 | (–HGT medium, no MTX) | 1.0 × 10⁻³ |
| 1 | (–HGT medium, no MTX) | 0.7 × 10⁻³ |

*t-PA in the culture medium was assayed quantitatively in a radioimmunoassay as follows: Purified t-PA and purified iodinated tracer t-PA derived from melanoma cells were diluted serially to include concentration of 12.5 to 400 ng/ml in a buffer containing phosphate buffered saline, pH 7.3, 0.5 percent bovine serum albumin, 0.01 percent Tween 80, and 0.02 percent NaN3. Appropriate dilutions of medium samples to be assayed were added to the radioactively labelled tracer proteins. The antigens were allowed to incubate overnight at room temperature in the presence of a 1:10,000 dilution of the IgG fraction of a rabbit anti-t-PA antiserum. Antibody-antigen complex was precipitated by absorption to goat anti-rabbit IgG Immunobeads (BioRad) for two hours at room temperature. The beads were cleared by the addition of saline diluent followed by centrifugation for ten minutes at 2000 × g at 4° Celsius. Supernatants were discarded and the radioactivity in the precipitates was monitored. Concentrations were assigned by comparison with the reference standard.

The cell lines are as follows: Cell line "1" is an unamplified clone from the original set of four. "1–15$_{500}$" is an amplified subclone of cell line "1" which was amplified initially in 50 nM MTX to give 1–15 and then transferred for further amplification into 500 nM MTX. 1–15$_{10,000}$ is subclone of 1–15$_{500}$ which has been further amplified in the presence of 10,000 nM MTX. Cell line 18B–9 is a subclone of one of the original four detected which had been amplified on 50 nM MTX.

A sample of CHO cell line 1–15$_{500}$ has been deposited with the American Type Culture Collection and accorded accession number CRL 9606.

All of the amplified cells show increased levels of t-PA production over that exhibited by the unamplified cell culture. Even the unamplified culture produces amounts of t-PA greater than 0.5 pg/cell/day; amplification results in levels approaching 50 ;g/cell/day.

F. Pharmaceutical Compositions

The compounds of the present invention can be formulated according to known methods to prepare pharmaceutically useful compositions, whereby the human tissue plasminogen activator product hereof is combined in admixture with a pharmaceutically acceptable carrier vehicle. Suitable vehicles and their formulation, inclusive of other human proteins, e.g. human serum albumin, are described for example in Remington's *Pharmaceutical Sciences* by E. W. Martin, which is hereby incorporated by reference. Such compositions will contain an effective amount of the protein hereof together with a suitable amount of vehicle in order to prepare pharmaceutically acceptable compositions suitable for effective administration to the host.

For example, the human tissue plasminogen activator hereof may be parenterally administered to subjects suffering from cardiovascular diseases or conditions. Dosage and dose rate may parallel that currently in use in clinical investigations of other cardiovascular, thrombolytic agents, e.g., about 440 IU/kg. body weight as an intravenous priming dose followed by a continuous intravenous infusion at about 440 IU/kg/hr. for 12 hours, in patients suffering from pulmonary embolism.

As one example of an appropriate dosage form for essentially homogeneous human tissue plasminogen activator in parenteral form applicable herein, a vial containing 25000 IU tissue plasminogen activator activity, 25 mg. mannitol and 45 mg. NaCl, may be reconstituted with 5 ml. sterile water for injection and mixed with a suitable volume of 0.9 percent Sodium Chloride Injection or 5 percent Dextrose Injection for intravenous administration.

G. Detailed Description of Recombinant Human t-PA

Figure 12:
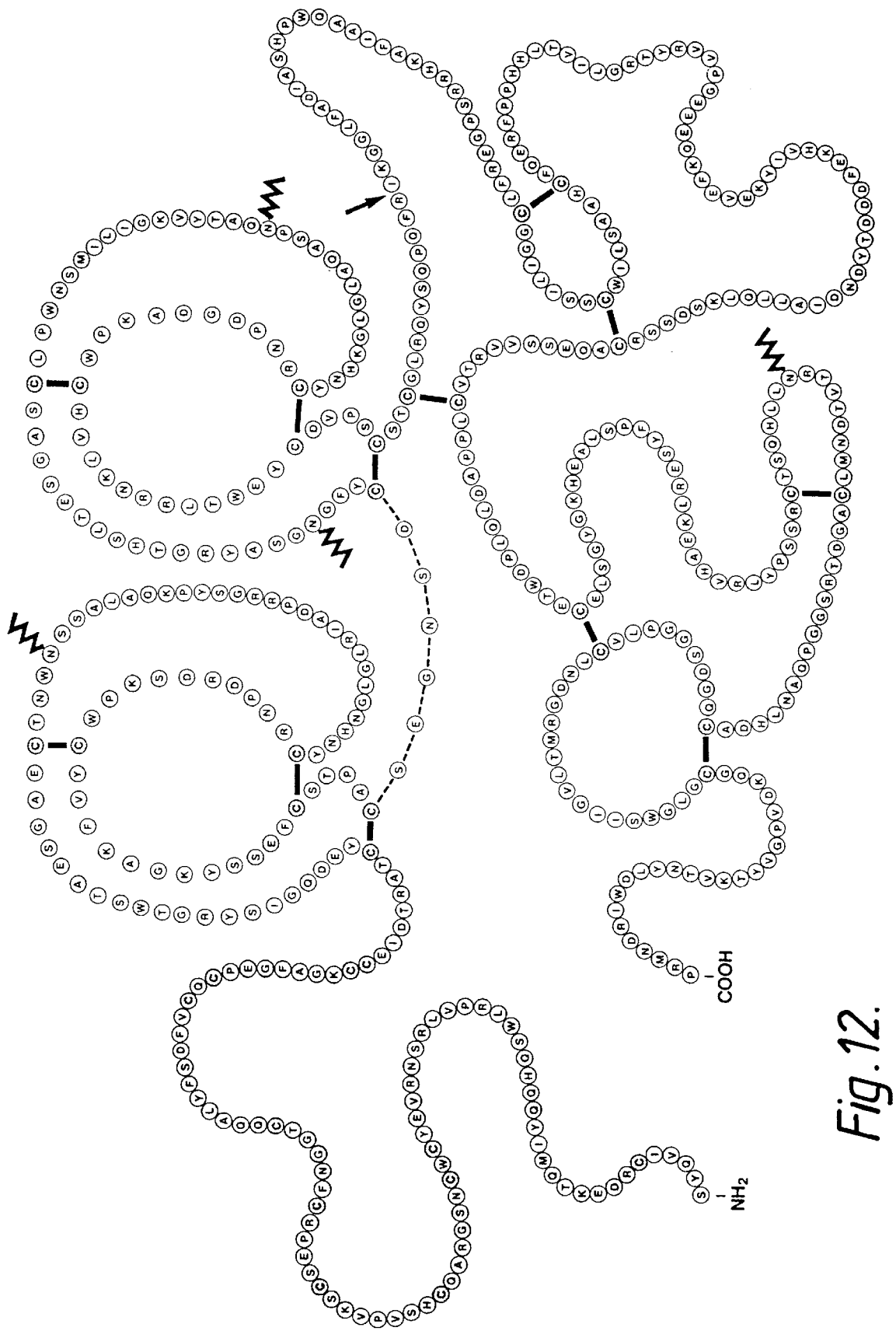
FIG. 12 is a schematic diagram of human tissue plasminogen activator as prepared by the method exemplified in E.1 herein.

The structure of the particular embodiment of human t-PA prepared in the examples herein has been studied in some detail, both by elucidation of the gene coding sequence and by protein biochemistry techniques. The current understanding of the protein structure is illustrated in FIG. 12.

It has also previously been demonstrated by Collen and coworkers (88) that two chain human t-PA is formed by proteolytic cleavage of the single chain molecule into two polypeptides connected by disulfide bonding. The present work permits the conclusion that the heavy chain (30882 mol. wt.) is derived from the $NH_2$ terminal part and the light chain (28126 ml. wt.) comprises the COOH-terminal region. N-terminal sequencing of the two chain molecule suggests that the two chain form is generated by cleavage of a single arginyl-isoleucine bond (FIG. 12; arrow depicted).

The primary structure of a portion of the heavy chain region of human t-PA (FIG. 12) reveals a high degree of sequence homology with the "kringle" regions of plasminogen (89) and prothrombin (40, 41). "Kringle" region refers to a characteristic triple disulfide structure originally discovered in the "pro"-fragment of prothrombin, first described in detail by Magnusson et al. (91, 92). From the primary sequence of t-PA, two so-called "kringle" regions, of 82 amino acids each, that share a high degree of homology with the 5 "kringle" regions of plasminogen are apparent. The remaining N-terminal 91 amino acids share little homology to the conventional "kringle" region. One can speculate however that this region may also assume a structure containing multiple disulfide bonds as 11 additional cysteine residues are found here.

The catalytic site of the light chain of human t-PA, the so-called serine protease region, as in other serine enzymes, is most likely formed by the $histidine_{322}$, $aspartic_{371}$ and serine478 residues. Furthermore, the amino acid sequences surrounding these residues are very homologous to corresponding parts of other serine proteases such as trypsin, prothrombin and plasminogen.

Notwithstanding that reference has been made to particular preferred embodiments, it will be understood that the present invention is not to be construed as limited to such, rather to the lawful scope of the appended claims.

BIBLIOGRAPHY

1. U.S. Pat. No. 3,355,361.
2. U.S. Pat. No. 3,926,727.
3. U.S. Pat. No. 4,029,767.
4. U.S. Pat. No. 4,258,030.
5. U.S. Pat. No. 4,271,150.
6. Eurpoean Patent Application Publn. No. 0037687.
7. Rijken, D. C., "Plasminogen Activator from Human Tissue," Krips Repro Meppel, 1980.
8. U.S. Pat. No. 3,555,000.
9. U.S. Pat. No. 3,998,947.
10. U.S. Pat. No. 4,245,051.
11. European Patent Application Publn. No. 0023860.
12. U.S. Pat. No. 4,083,961.
13. U.S. Pat. No. 4,177,262.
14. U.S. Pat. No. 4,082,612.
15. Wallen, P., *Proc. Serono Symp.* 9, 91 (1977).
16. Thorsen, S., et al., *Thrombos. Diathes. haemorrh.* 28, 65 (1972).
17. Collen, *Thrombos. Haemostas.* 43, 77 (1980).
18. Wiman et al., *Nature* 272, 549 (1978).
19. European Patent Application Publn. No. 0041766.
20. Weimar, W., et al., *The Lancet* Vol. II, No. 8254, p. 1018 (1981).
21. British Patent Application Publn. No. 2007676A.
22. Wetzel, *American Scientist* 68, 664 (1980).
23. *Microbiology,* 2d Ed., Harper and Row Publications, Inc., Hagerstown, Md. (1973), est. pp. 1122 et seq.
24. *Scientific American* 245, 106 (1981).
25. British Patent Application Publn. No. 2055382A.
26. German Offenlegungsschrift 2644432.
27. Chang et al., *Nature* 275, 617 (1978).
28. Itakura et al., *Science* 198, 1056 (1977).
29. Goeddel et al., *Nucleic Acids Research* 8, 4057 (1980).
30. European Patent Application Publn. No. 0036776.
31. Siebenlist et al., *Cell* 20, 269 (1980).
32. Stinchcomb et al., *Nature* 282, 39 (1979).
33. Kingsman et al., *Gene* 7, 141 (1979).
34. Tschumper et al., *Gene* 10, 157 (1980).
35. Mortimer et al., *Microbiological Reviews* 44, 519 (1980).
36. Miozzari et al., *Journal of Bacteriology* 134, 48 (1978).
37. Jones, *Genetics* 85, 23 (1977).
38. Hitzeman, et al., *J. Biol. Chem.* 255, 12073 (1980).
39. Hess et al., *J. Adv. Enzyme Regul.* 7, 149 (1968).
40. Holland et al., *Biochemistry* 17, 4900 (1978).
41. Bostian et al., *Proc. Natl. Acad. Sci. (U.S.A.)* 77, 4504 (1980).
42. *The Molecular Biology of Yeast* (Aug. 11–18, 1981), Cold Spring Harbor Laboratory, Cold Spring Harbor, New York.
43. Chambon, *Ann. Rev. Biochemistry,* 44, 613 (1975).
44. *Tissue Culture,* Academic Press, Kruse and Patterson eds., (1973).
45. Gluzman, *Cell* 23, 175 (1981).
46. Bolivar et al., *Gene* 2, 95 (1977).
47. Lusky et al., *Nature* 293, 79 (1981).
48. Gluzman et al., Cold Spring Harbor Symp. Quant. Biol. 44, 293 (1980).
49. Fiers et al., *Nature* 273, 113 (1978).

50. Reddy et al., *Science* 200, 494 (1978).
51. Crea et al., *Nucleic Acids Research* 8, 2331 (1980).
52. Goeddel et al., *Nature* 287, 411 (1980).
53. Gray et al., *Nature* 295, 503 (1982).
54. Oppermann et al., *Virology* 108, 47 (1981).
55. Ward et al., *J. Virol.* 9, 61 (1972).
56. Aviv et al., *Proc. Natl. Acad. Sci. (U.S.A.)* 69, 1408 (1972).
57. Lehrach et al., *Biochemistry* 16, 4743 (1977).
58. Lynch et al., *Virology* 98, 251 (1979).
59. Lodish, *Am. Rev. of Biochem.* 45, 40 (1976).
60. Pelham et al., *Eur. J. Biochem.* 43, 247 (1974).
61. Blobel, et al., *J. Cell Biology* 67, 852 (1975).
62. Shields et al., *J. Biol. Chemistry* 253, 3753 (1978).
63. Laemmli, *Nature* 227, 680 (1970).
64. Bonner et al., *Eur. J. Biochem.* 46, 83 (1974).
65. Goeddel et al., *Nature* 281, 544 (1979).
66. Wickens et al., *J. Biol. Chem.* 253, 2483 (1978).
67. Chang et al., *Nature* 275, 617 (1978).
68. Boliver et al., *Gene* 2, 95 (1977).
69. Grunstein et al., *Proc. Natl. Acad. Sci. U.S.A.* 72, 3961 (1975).
70. Hanahan et al., *Gene* 10, 63 (1980).
71. Birnboim et al., *Nucleic Acids Res.* 7, 1513 (1979).
72. Smith, *Methods Enzymol.* 65, 499 (1980).
73. Messing et al., *Nucleic Acids Res.* 9, 309 (1981).
74. Maxam et al., *Methods in Enzymol.* 65. 499 (1980).
75. Crea et al., *Proc. Natl. Acad. Sci.* 75, 5765 (1978).
76. Lawn et al., *Cell* 15, 1157 (1978).
77. Southern, *J. Mol. Biol.* 98, 503 (1975).
78. Benton et al., *Science* 196, 180 (1977).
79. McGrath and Levinson, *Nature* 295, 423 (1982).
80. Blin et al., *Nucleic Acid Res.* 3, 2303 (1976).
81. Lawn et al., *Science* 212, 1159 (1981).
82. Fritsch et al., *Cell* 19, 959 (1980).
83. Taylor et al., *Biochim. Biophys. Acta* 442, 324 (1976).
83b. Edman et al., *European J. Biochem.* 1, 80 (1967).
84. Denhardt, *Biochem. Biophys. Res. Comm.* 23, 641 (1966).
85. Wahl et al., *Proc. Natl. Acad. Sci. (U.S.A.)* 76, 3683 (1979).
86. Davis et al., Advanced Bacterial Genetics, Cold Spring Harbor Laboratory, New York (1980).
87. Granelli-Piperno et al., *J. Exp. Med.* 148, 223 (1978).
88. Rijken et al., *J. Biol. Chem.* 256, 7035 (1981).
89. Sottrup-Jensen et al., *Progress in Chemical Fibrinolysis and Thrombolysis,* Vol. 3, Raven Press, N.Y. p. 191 (1978)
90. Sothrup-Jensen et al., *Proc. Natl. Acad. Sci. (U.S.A.)* 72, 2577 (1975).
91. Magnussen et al., *Proteolysis and Physiological Regulation,* Ribbons et al., Eds., Academic Press, New York, p. 203 (1976).
92. Magnussen et al., *Proteases and Biological Control,* Cold Spring Harbor Laboratory, N.Y., p. 123 (1975).
93. Miller, Experiments in Molecular Genetics, p. 431–3, Cold Spring Harbor Lab., Cold Spring Harbor, N.Y. (1972).
94. Reich, E., *Proteases and Biological Control,* (Ibid) p. 333–341.
95. Matsuo, O., et al., *Throm. Haemostasis* 45, 225 (1981).
96. Koringer, C., et al., *Throm. Haemostasis* 46 561, 662 (1981).
97. Hoylaerts, M., et al., *J. Biol. Chem.* 257 2912 (1982).
98. Koringer, C., et al., *Thromb. Haemostasis* 46, 685 (1981).

What is claimed is:

1. A method for treating a vascular disease or condition requiring thrombolytic therapy comprising administering to a subject suffering from said disease or condition an effective amount of a tissue plasminogen activator (t-PA) as produced by recombinant expression of DNA encoding said tissue plasminogen activator in transformed host cells, in admixture with a pharmaceutically acceptable excipient.

2. The method according to claim 1 wherein said transformed host cells are mammalian cells.

3. The method according to claim 2 wherein said mammalian cells are Chinese hamster ovary (CHO) cells.

4. The method according to claim 1 wherein said transformed host cells are bacterial cells.

5. The method according to claim 4 wherein said bacterial host cells are *E. coli* cells.

6. The method according to claim 1 wherein said disease or condition requiring thrombolytic therapy is a cardiovascular disease or condition.

7. The method according to claim 6 wherein said cardiovascular condition is pulmonary embolism.

8. The method according to claim 1 wherein said t-PA is administered parenterally.

9. The method according to claim 8 wherein said t-PA is administered intravenously.

10. The method according to claim 7 wherein said t-PA is administered as an intravenous priming dose of about 440 IU/KG body weight, followed by a continuous intravenous infusion at about 440 IU/kg/hr for 12 hours.

11. The method according to claim 1 wherein said t-PA comprises the amino acid sequence 1 to 527 set forth in combined FIGS. 5A, 5B and 5C thereof.

12. The method according to claim 1 wherein said t-PA comprises the amino acid sequence 69 to 527 set forth in combined FIGS. 5A, 5B and 5C hereof.

13. The method according to claim 1 wherein said t-PA demonstrates higher affinity for fibrin compared with urokinase.

14. The method according to claim 1 wherein said t-PA is unaccompanied by native glycosylation.

* * * * *